United States Patent
Kim et al.

(10) Patent No.: US 10,779,885 B2
(45) Date of Patent: Sep. 22, 2020

(54) APPARATUS AND METHODS FOR THE TREATMENT OF TISSUE USING MICROWAVE ENERGY

(71) Applicant: MIRADRY. INC., Santa Clara, CA (US)

(72) Inventors: Steven Kim, Los Altos, CA (US); Ted Su, Sunnyvale, CA (US); Daniel Francis, Mountain View, CA (US); Jessi Ernest Johnson, Sunnyvale, CA (US); Donghoon Chun, Sunnyvale, CA (US)

(73) Assignee: MIRADRY. INC., Santa Clara, CA (US)

( * ) Notice: Subject to any disclaimer, the term of this patent is extended or adjusted under 35 U.S.C. 154(b) by 947 days.

(21) Appl. No.: 14/907,145

(22) PCT Filed: Jul. 24, 2014

(86) PCT No.: PCT/US2014/047996
§ 371 (c)(1),
(2) Date: Jan. 22, 2016

(87) PCT Pub. No.: WO2015/013502
PCT Pub. Date: Jan. 29, 2015

(65) Prior Publication Data
US 2016/0157934 A1 Jun. 9, 2016

Related U.S. Application Data
(60) Provisional application No. 61/858,050, filed on Jul. 24, 2013.

(51) Int. Cl.
*A61B 18/00* (2006.01)
*A61B 18/18* (2006.01)
*A61N 5/04* (2006.01)

(52) U.S. Cl.
CPC ........... *A61B 18/1815* (2013.01); *A61N 5/04* (2013.01); *A61B 2018/00452* (2013.01)

(58) Field of Classification Search
CPC ........ A61B 18/1815; A61B 2018/0045; A61N 5/04
See application file for complete search history.

(56) References Cited

U.S. PATENT DOCUMENTS

| 2,407,690 A | 9/1946 | Southworth |
| 3,307,553 A | 3/1967 | Liebner |

(Continued)

FOREIGN PATENT DOCUMENTS

| AU | 297299 A | 9/1999 |
| CN | 1688363 A | 10/2005 |

(Continued)

OTHER PUBLICATIONS

Kim, Jaehoon, Implanted Antennas Inside a Human Body: Simulations, Designs, and Characterizations, IEEE Transactions on Microwave Theory and Techniques, vol. 52, No. 8, Aug. 2004 (Year: 2004).*

(Continued)

*Primary Examiner* — Kaitlyn E Smith
*Assistant Examiner* — Yasamin Ekrami
(74) *Attorney, Agent, or Firm* — Baker & McKenzie

(57) ABSTRACT

Systems and methods for delivering microwave energy to skin are provided, such that a focal zone of destructive heat is generated in the upper sub-dermis, mid-dermis, and/or lower dermis. This microwave therapy may be used for hair removal, treatment of acne, skin tightening, treatment of toe nail fungus, or sweat reduction. According to one embodiment, a system can include a microwave applicator having a distal treatment portion that includes at least one microwave antenna, a cooling system, and vacuum features. In (Continued)

some embodiments, the interaction between incident waves transmitted from the microwave applicator and reflected waves may be used to generate a standing wave with a peak energy density in selected regions of the dermis.

9 Claims, 11 Drawing Sheets

(56) References Cited

U.S. PATENT DOCUMENTS

| | | |
|---|---|---|
| 3,527,227 A | 9/1970 | Fritz |
| 3,693,623 A | 9/1972 | Harte et al. |
| 3,845,267 A | 10/1974 | Fitzmayer |
| 4,069,827 A | 1/1978 | Dominy |
| 4,095,602 A | 6/1978 | Leveen |
| 4,108,147 A | 8/1978 | Kantor |
| 4,140,130 A | 2/1979 | Storm, III |
| 4,174,713 A | 11/1979 | Mehl |
| 4,190,053 A | 2/1980 | Sterzer |
| 4,190,056 A | 2/1980 | Tapper et al. |
| 4,197,860 A | 4/1980 | Sterzer |
| 4,228,809 A | 10/1980 | Paglione |
| 4,292,960 A | 10/1981 | Paglione |
| 4,332,260 A | 6/1982 | Bicher et al. |
| 4,375,220 A | 3/1983 | Matvias |
| 4,378,806 A | 4/1983 | Henley Cohn |
| 4,388,924 A | 6/1983 | Weissman et al. |
| 4,397,313 A | 8/1983 | Vaguine |
| 4,397,314 A | 8/1983 | Vaguine |
| 4,446,874 A | 5/1984 | Vaguine |
| 4,528,991 A | 7/1985 | Dittmar et al. |
| 4,589,424 A | 5/1986 | Vaguine |
| 4,597,379 A | 7/1986 | Kihn et al. |
| 4,614,191 A | 9/1986 | Perler |
| 4,617,926 A | 10/1986 | Sutton |
| 4,632,128 A | 12/1986 | Paglione et al. |
| 4,641,649 A | 2/1987 | Walinsky et al. |
| 4,669,475 A | 6/1987 | Turner |
| 4,672,980 A | 6/1987 | Turner |
| 4,690,156 A | 9/1987 | Kikuchi et al. |
| 4,702,262 A | 10/1987 | Andersen et al. |
| 4,744,372 A | 5/1988 | Kikuchi et al. |
| 4,747,416 A | 5/1988 | Kikuchi et al. |
| 4,794,930 A | 1/1989 | Machida et al. |
| 4,798,215 A | 1/1989 | Turner |
| 4,800,899 A | 1/1989 | Elliott |
| 4,825,880 A | 5/1989 | Stauffer et al. |
| 4,841,989 A | 6/1989 | Kikuchi et al. |
| 4,841,990 A | 6/1989 | Kikuchi et al. |
| 4,860,752 A | 8/1989 | Turner |
| 4,881,543 A | 11/1989 | Trembly et al. |
| 4,891,483 A | 1/1990 | Kikuchi et al. |
| 4,945,912 A | 8/1990 | Langberg |
| 4,974,587 A | 12/1990 | Turner et al. |
| 5,059,192 A | 10/1991 | Zaias |
| 5,097,846 A | 3/1992 | Larsen |
| 5,101,836 A | 4/1992 | Lee |
| 5,107,832 A | 4/1992 | Guibert et al. |
| 5,143,063 A | 9/1992 | Fellner |
| 5,186,181 A | 2/1993 | Franconi et al. |
| 5,190,518 A | 3/1993 | Takasu |
| 5,198,776 A | 3/1993 | Carr |
| 5,226,907 A | 7/1993 | Tankovich |
| 5,234,004 A | 8/1993 | Hascoet et al. |
| 5,246,438 A | 9/1993 | Langberg |
| 5,272,301 A | 12/1993 | Finger et al. |
| 5,295,955 A | 3/1994 | Rosen et al. |
| 5,301,692 A | 4/1994 | Knowlton |
| 5,305,748 A | 4/1994 | Wilk |
| 5,315,994 A | 5/1994 | Guibert et al. |
| 5,316,000 A | 5/1994 | Chapelon et al. |
| 5,364,336 A | 11/1994 | Carr |
| 5,364,394 A | 11/1994 | Mehl |
| 5,383,917 A | 1/1995 | Desai et al. |
| 5,385,544 A | 1/1995 | Edwards et al. |
| 5,405,346 A | 4/1995 | Grundy et al. |
| 5,407,440 A | 4/1995 | Zinreich et al. |
| 5,409,484 A | 4/1995 | Erlich et al. |
| 5,421,819 A | 6/1995 | Edwards et al. |
| 5,425,728 A | 6/1995 | Tankovich |
| 5,431,650 A | 7/1995 | Cosmescu |
| 5,433,740 A | 7/1995 | Yamaguchi |
| 5,441,532 A | 8/1995 | Fenn |
| 5,443,487 A | 8/1995 | Guibert et al. |
| 5,462,521 A | 10/1995 | Brucker et al. |
| 5,474,071 A | 12/1995 | Chapelon et al. |
| 5,503,150 A | 4/1996 | Evans |
| 5,507,741 A | 4/1996 | L'Esperance, Jr. |
| 5,507,790 A | 4/1996 | Weiss |
| 5,509,929 A | 4/1996 | Hascoet et al. |
| 5,522,814 A | 6/1996 | Bernaz |
| 5,531,662 A | 7/1996 | Carr |
| 5,540,681 A | 7/1996 | Strul et al. |
| 5,549,639 A | 8/1996 | Ross |
| 5,553,612 A | 9/1996 | Lundback |
| 5,569,237 A | 10/1996 | Beckenstein |
| 5,571,154 A | 11/1996 | Ren |
| 5,575,789 A | 11/1996 | Bell et al. |
| 5,584,830 A | 12/1996 | Ladd et al. |
| 5,586,981 A | 12/1996 | Hu |
| 5,595,568 A | 1/1997 | Anderson et al. |
| 5,649,973 A | 7/1997 | Tierney et al. |
| 5,660,836 A | 8/1997 | Knowlton |
| 5,662,110 A | 9/1997 | Carr |
| 5,669,916 A | 9/1997 | Anderson |
| 5,674,219 A | 10/1997 | Monson et al. |
| 5,683,381 A | 11/1997 | Carr et al. |
| 5,683,382 A | 11/1997 | Lenihan et al. |
| 5,690,614 A | 11/1997 | Carr et al. |
| 5,707,403 A | 1/1998 | Grove et al. |
| 5,724,966 A | 3/1998 | Lundback |
| 5,733,269 A | 3/1998 | Fuisz |
| 5,735,844 A | 4/1998 | Anderson et al. |
| 5,742,392 A | 4/1998 | Anderson et al. |
| 5,743,899 A | 4/1998 | Zinreich |
| 5,755,753 A | 5/1998 | Knowlton |
| 5,769,879 A | 6/1998 | Richards et al. |
| 5,776,127 A | 7/1998 | Anderson et al. |
| 5,782,897 A | 7/1998 | Carr |
| 5,810,801 A | 9/1998 | Anderson et al. |
| 5,810,804 A | 9/1998 | Gough et al. |
| 5,814,996 A | 9/1998 | Winter |
| 5,824,023 A | 10/1998 | Anderson |
| 5,830,208 A | 11/1998 | Muller |
| 5,836,999 A | 11/1998 | Eckhouse et al. |
| 5,868,732 A | 2/1999 | Waldman et al. |
| 5,879,346 A | 3/1999 | Waldman et al. |
| 5,891,094 A | 4/1999 | Masterson et al. |
| 5,897,549 A | 4/1999 | Tankovich |
| 5,902,263 A | 5/1999 | Patterson et al. |
| 5,904,709 A | 5/1999 | Arndt et al. |
| 5,919,218 A | 7/1999 | Carr |
| 5,928,797 A | 7/1999 | Vineberg |
| 5,931,860 A | 8/1999 | Reid et al. |
| 5,949,845 A | 9/1999 | Sterzer |
| 5,971,982 A | 10/1999 | Betsill et al. |
| 5,979,454 A | 11/1999 | Anvari et al. |
| 5,983,124 A | 11/1999 | Carr |
| 5,983,900 A | 11/1999 | Clement et al. |
| 5,989,245 A | 11/1999 | Pescott |
| 6,015,404 A | 1/2000 | Altshuler et al. |
| 6,024,095 A | 2/2000 | Stanley, III |
| 6,026,331 A | 2/2000 | Feldberg et al. |
| 6,026,816 A | 2/2000 | McMillan et al. |
| 6,030,378 A | 2/2000 | Stewart |
| 6,036,632 A | 3/2000 | Whitmore, III et al. |
| 6,047,215 A | 4/2000 | McClure et al. |
| 6,050,990 A | 4/2000 | Tankovich et al. |
| 6,077,294 A | 6/2000 | Cho et al. |
| 6,080,146 A | 6/2000 | Altshuler et al. |
| 6,093,186 A | 7/2000 | Goble |
| 6,097,985 A | 8/2000 | Kasevich et al. |
| 6,104,959 A | 8/2000 | Spertell |

(56) References Cited

U.S. PATENT DOCUMENTS

| | | |
|---|---|---|
| 6,106,514 A | 8/2000 | O'Donnell, Jr. |
| 6,113,559 A | 9/2000 | Klopotek |
| 6,113,593 A | 9/2000 | Tu et al. |
| 6,126,636 A | 10/2000 | Naka |
| 6,129,696 A | 10/2000 | Sibalis |
| 6,139,569 A | 10/2000 | Ingle et al. |
| 6,149,644 A | 11/2000 | Xie |
| 6,162,212 A | 12/2000 | Kreindel et al. |
| 6,162,218 A | 12/2000 | Elbrecht et al. |
| 6,171,301 B1 | 1/2001 | Nelson et al. |
| 6,175,768 B1 | 1/2001 | Arndt et al. |
| 6,181,970 B1 | 1/2001 | Kasevich |
| 6,183,773 B1 | 2/2001 | Anderson |
| 6,187,001 B1 | 2/2001 | Azar et al. |
| 6,197,020 B1 | 3/2001 | O'Donnell, Jr. |
| 6,208,903 B1 | 3/2001 | Richards et al. |
| 6,210,367 B1 | 4/2001 | Carr |
| 6,214,034 B1 | 4/2001 | Azar |
| 6,223,076 B1 | 4/2001 | Tapper |
| 6,231,569 B1 | 5/2001 | Bek et al. |
| 6,235,016 B1 | 5/2001 | Stewart |
| 6,241,753 B1 | 6/2001 | Knowlton |
| 6,245,062 B1 | 6/2001 | Berube et al. |
| 6,264,652 B1 | 7/2001 | Eggers et al. |
| 6,273,884 B1 | 8/2001 | Altshuler et al. |
| 6,277,104 B1 | 8/2001 | Lasko et al. |
| 6,277,111 B1 | 8/2001 | Clement et al. |
| 6,277,116 B1 | 8/2001 | Utely et al. |
| 6,280,441 B1 | 8/2001 | Ryan |
| 6,283,956 B1 | 9/2001 | McDaniel |
| 6,283,987 B1 | 9/2001 | Laird et al. |
| 6,287,302 B1 | 9/2001 | Berube |
| 6,290,699 B1 | 9/2001 | Hall et al. |
| 6,293,941 B1 | 9/2001 | Strul et al. |
| 6,306,128 B1 | 10/2001 | Waldman et al. |
| 6,306,130 B1 | 10/2001 | Anderson et al. |
| 6,319,211 B1 | 11/2001 | Ito et al. |
| 6,322,584 B2 | 11/2001 | Ingle et al. |
| 6,325,769 B1 | 12/2001 | Klopotek |
| 6,325,796 B1 | 12/2001 | Berube et al. |
| 6,330,479 B1 | 12/2001 | Stauffer |
| 6,334,074 B1 | 12/2001 | Spertell |
| 6,347,251 B1 | 2/2002 | Deng |
| 6,350,263 B1 | 2/2002 | Wetzig et al. |
| 6,350,276 B1 | 2/2002 | Knowlton |
| 6,361,531 B1 | 3/2002 | Hissong |
| 6,364,876 B1 | 4/2002 | Erb et al. |
| 6,383,176 B1 | 5/2002 | Connors et al. |
| 6,387,103 B2 | 5/2002 | Shadduck |
| 6,402,739 B1 | 6/2002 | Neev |
| 6,409,720 B1 | 6/2002 | Hissong et al. |
| 6,409,722 B1 | 6/2002 | Hoey et al. |
| 6,413,253 B1 | 7/2002 | Koop et al. |
| 6,413,254 B1 | 7/2002 | Hissong et al. |
| 6,413,255 B1 | 7/2002 | Stern |
| 6,427,089 B1 | 7/2002 | Knowlton |
| 6,428,532 B1 | 8/2002 | Doukas et al. |
| 6,430,446 B1 | 8/2002 | Knowlton |
| 6,436,094 B1 | 8/2002 | Reuter |
| 6,436,127 B1 | 8/2002 | Anderson et al. |
| 6,443,914 B1 | 9/2002 | Costantino |
| 6,443,946 B2 | 9/2002 | Clement et al. |
| 6,451,013 B1 | 9/2002 | Bays et al. |
| 6,451,015 B1 | 9/2002 | Rittman, III et al. |
| 6,457,476 B1 | 10/2002 | Elmer et al. |
| 6,461,378 B1 | 10/2002 | Knowlton |
| 6,468,235 B2 | 10/2002 | Ito et al. |
| 6,470,216 B1 | 10/2002 | Knowlton |
| 6,471,662 B1 | 10/2002 | Jaggy et al. |
| 6,471,696 B1 | 10/2002 | Berube et al. |
| 6,475,179 B1 | 11/2002 | Wang et al. |
| 6,475,211 B2 | 11/2002 | Chess et al. |
| 6,480,746 B1 | 11/2002 | Ingle et al. |
| 6,485,484 B1 | 11/2002 | Connors et al. |
| 6,485,703 B1 | 11/2002 | Coté et al. |
| 6,500,141 B1 | 12/2002 | Irion et al. |
| 6,508,813 B1 | 1/2003 | Altshuler |
| 6,514,250 B1 | 2/2003 | Jahns et al. |
| 6,517,532 B1 | 2/2003 | Altshuler et al. |
| 6,529,778 B2 | 3/2003 | Prutchi |
| 6,558,382 B2 | 5/2003 | Jahns et al. |
| 6,575,969 B1 | 6/2003 | Rittman, III et al. |
| 6,577,903 B1 | 6/2003 | Cronin et al. |
| 6,584,360 B2 | 6/2003 | Francischelli et al. |
| 6,585,733 B2 | 7/2003 | Wellman |
| 6,595,934 B1 | 7/2003 | Hissong et al. |
| 6,600,951 B1 | 7/2003 | Anderson |
| 6,605,080 B1 | 8/2003 | Altshuler et al. |
| 6,607,498 B2 | 8/2003 | Eshel |
| 6,626,854 B2 | 9/2003 | Friedman et al. |
| 6,628,990 B1 | 9/2003 | Habib et al. |
| 6,629,974 B2 | 10/2003 | Penny et al. |
| 6,645,162 B2 | 11/2003 | Friedman et al. |
| 6,648,904 B2 | 11/2003 | Altshuler et al. |
| 6,652,518 B2 | 11/2003 | Wellman et al. |
| 6,653,618 B2 | 11/2003 | Zenzie |
| 6,662,054 B2 | 12/2003 | Kreindel et al. |
| 6,663,659 B2 | 12/2003 | McDaniel |
| 6,676,654 B1 | 1/2004 | Balle Petersen et al. |
| 6,676,655 B2 | 1/2004 | McDaniel |
| 6,682,501 B1 | 1/2004 | Nelson et al. |
| 6,692,450 B1 | 2/2004 | Coleman |
| 6,723,090 B2 | 4/2004 | Altshuler et al. |
| 6,725,095 B2 | 4/2004 | Fenn et al. |
| 6,736,810 B2 | 5/2004 | Hoey et al. |
| 6,743,222 B2 | 6/2004 | Durkin et al. |
| 6,763,836 B2 | 7/2004 | Tasto et al. |
| 6,766,202 B2 | 7/2004 | Underwood et al. |
| 6,807,446 B2 | 10/2004 | Fenn et al. |
| 6,808,532 B2 | 10/2004 | Andersen et al. |
| 6,821,274 B2 | 11/2004 | McHale et al. |
| 6,823,216 B1 | 11/2004 | Salomir et al. |
| 6,824,542 B2 | 11/2004 | Jay |
| 6,856,839 B2 | 2/2005 | Litovitz |
| 6,861,954 B2 | 3/2005 | Levin |
| 6,878,144 B2 | 4/2005 | Altshuler et al. |
| 6,878,147 B2 | 4/2005 | Prakash et al. |
| 6,881,212 B1 | 4/2005 | Clement et al. |
| 6,887,239 B2 | 5/2005 | Elstrom et al. |
| 6,887,260 B1 | 5/2005 | McDaniel |
| 6,888,319 B2 | 5/2005 | Inochkin et al. |
| 6,897,238 B2 | 5/2005 | Anderson |
| 6,907,879 B2 | 6/2005 | Drinan et al. |
| 6,916,316 B2 | 7/2005 | Jay |
| 6,918,908 B2 | 7/2005 | Bonner et al. |
| 6,939,344 B2 | 9/2005 | Kreindel |
| 6,939,346 B2 | 9/2005 | Kannenberg et al. |
| 6,955,672 B2 | 10/2005 | Cense et al. |
| 6,974,415 B2 | 12/2005 | Cerwin et al. |
| 6,976,984 B2 | 12/2005 | Cense et al. |
| 6,997,923 B2 | 2/2006 | Anderson et al. |
| 7,006,874 B2 | 2/2006 | Knowlton et al. |
| 7,022,121 B2 | 4/2006 | Stern et al. |
| 7,029,469 B2 | 4/2006 | Vastly |
| 7,033,352 B1 | 4/2006 | Gauthier et al. |
| 7,044,959 B2 | 5/2006 | Anderson et al. |
| 7,056,318 B2 | 6/2006 | Black |
| 7,066,929 B1 | 6/2006 | Azar et al. |
| 7,074,218 B2 | 7/2006 | Washington et al. |
| 7,081,111 B2 | 7/2006 | Svaasand et al. |
| 7,089,054 B2 | 8/2006 | Patti |
| 7,107,997 B1 | 9/2006 | Moses et al. |
| 7,115,123 B2 | 10/2006 | Knowlton et al. |
| 7,118,590 B1 | 10/2006 | Cronin |
| 7,122,029 B2 | 10/2006 | Koop et al. |
| 7,128,739 B2 | 10/2006 | Prakash et al. |
| 7,135,033 B2 | 11/2006 | Altshuler et al. |
| 7,136,699 B2 | 11/2006 | Palti |
| 7,141,049 B2 | 11/2006 | Stern et al. |
| 7,151,964 B2 | 12/2006 | Desai et al. |
| 7,153,256 B2 | 12/2006 | Riehl et al. |
| 7,153,285 B2 | 12/2006 | Lauman et al. |
| 7,162,291 B1 | 1/2007 | Nachaliel |
| 7,163,536 B2 | 1/2007 | Godara |

(56) References Cited

U.S. PATENT DOCUMENTS

| | | |
|---|---|---|
| 7,175,950 B2 | 2/2007 | Anderson et al. |
| 7,189,230 B2 | 3/2007 | Knowlton |
| 7,192,429 B2 | 3/2007 | Trembly |
| 7,204,832 B2 | 4/2007 | Altshuler et al. |
| 7,217,265 B2 | 5/2007 | Hennings et al. |
| 7,220,254 B2 | 5/2007 | Altshuler et al. |
| 7,220,778 B2 | 5/2007 | Anderson et al. |
| 7,229,436 B2 | 6/2007 | Stern et al. |
| 7,234,739 B2 | 6/2007 | Saitoh et al. |
| 7,238,182 B2 | 7/2007 | Swoyer et al. |
| 7,241,291 B2 | 7/2007 | Kreindel et al. |
| 7,247,155 B2 | 7/2007 | Hoey et al. |
| 7,250,047 B2 | 7/2007 | Anderson et al. |
| 7,252,628 B2 | 8/2007 | Van Hal et al. |
| 7,258,674 B2 | 8/2007 | Cribbs et al. |
| 7,267,675 B2 | 9/2007 | Stern et al. |
| 7,276,058 B2 | 10/2007 | Altshuler et al. |
| 7,290,326 B2 | 11/2007 | Dutton |
| 7,309,335 B2 | 12/2007 | Altshuler et al. |
| 7,311,674 B2 | 12/2007 | Gingrich et al. |
| 7,329,273 B2 | 2/2008 | Altshuler et al. |
| 7,329,274 B2 | 2/2008 | Altshuler et al. |
| 7,331,951 B2 | 2/2008 | Eshel et al. |
| 7,344,587 B2 | 3/2008 | Khan et al. |
| 7,347,855 B2 | 3/2008 | Eshel et al. |
| 7,351,252 B2 | 4/2008 | Altshuler et al. |
| 7,354,448 B2 | 4/2008 | Altshuler et al. |
| 7,367,341 B2 | 5/2008 | Anderson et al. |
| 7,377,917 B2 | 5/2008 | Trembly |
| 7,399,297 B2 | 7/2008 | Ikadai et al. |
| 7,422,586 B2 | 9/2008 | Morris et al. |
| 7,422,598 B2 | 9/2008 | Altshuler et al. |
| 7,431,718 B2 | 10/2008 | Ikadai |
| 7,470,270 B2 | 12/2008 | Azar et al. |
| 7,479,101 B2 | 1/2009 | Hunter et al. |
| 7,481,807 B2 | 1/2009 | Knudsen et al. |
| 7,491,171 B2 | 2/2009 | Barthe et al. |
| 7,524,328 B2 | 4/2009 | Connors et al. |
| 7,530,356 B2 | 5/2009 | Slayton et al. |
| 7,530,958 B2 | 5/2009 | Slayton et al. |
| 7,540,869 B2 | 6/2009 | Altshuler et al. |
| 7,544,204 B2 | 6/2009 | Krespi et al. |
| 7,565,207 B2 | 7/2009 | Turner et al. |
| 7,568,619 B2 | 8/2009 | Todd et al. |
| 7,588,547 B2 | 9/2009 | Deem et al. |
| 7,599,745 B2 | 10/2009 | Palti |
| 7,601,128 B2 | 10/2009 | Deem et al. |
| 7,613,523 B2 | 11/2009 | Eggers et al. |
| 7,630,774 B2 | 12/2009 | Karni et al. |
| 7,643,883 B2 | 1/2010 | Kreindel |
| 7,682,321 B2 | 3/2010 | Naldoni |
| 7,713,234 B2 | 5/2010 | Karanzas |
| 7,722,535 B2 | 5/2010 | Randlov et al. |
| 7,722,600 B2 | 5/2010 | Connors et al. |
| 7,722,656 B1 | 5/2010 | Segal |
| 7,736,360 B2 | 6/2010 | Mody et al. |
| 7,740,600 B2 | 6/2010 | Slatkine et al. |
| 7,740,651 B2 | 6/2010 | Barak et al. |
| 7,749,260 B2 | 7/2010 | Da Silva et al. |
| 7,758,524 B2 | 7/2010 | Barthe et al. |
| 7,758,537 B1 | 7/2010 | Brunell et al. |
| 7,762,964 B2 | 7/2010 | Slatkine |
| 7,763,060 B2 | 7/2010 | Baumann |
| 7,771,421 B2 | 8/2010 | Stewart et al. |
| 7,799,019 B2 | 9/2010 | Turovskiy et al. |
| 7,805,201 B2 | 9/2010 | Palti |
| 7,815,570 B2 | 10/2010 | Eshel et al. |
| 7,815,633 B2 | 10/2010 | Zanelli et al. |
| 7,824,394 B2 | 11/2010 | Manstein |
| 7,828,734 B2 | 11/2010 | Azhari et al. |
| 7,837,694 B2 | 11/2010 | Tethrake et al. |
| 7,842,029 B2 | 11/2010 | Anderson et al. |
| 7,854,754 B2 | 12/2010 | Ting et al. |
| 7,857,773 B2 | 12/2010 | Desilets et al. |
| 7,857,775 B2 | 12/2010 | Rosenberg et al. |
| 7,862,564 B2 | 1/2011 | Goble |
| 7,864,129 B2 | 1/2011 | Konishi |
| 7,891,362 B2 | 2/2011 | Domankevitz et al. |
| 7,905,844 B2 | 3/2011 | Desilets et al. |
| 8,073,550 B1 | 12/2011 | Spertell |
| 8,211,099 B2 | 7/2012 | Buysse et al. |
| 8,343,145 B2 | 1/2013 | Brannan |
| 8,367,959 B2 | 2/2013 | Spertell |
| 8,394,092 B2 | 3/2013 | Brannan |
| 8,401,668 B2 | 3/2013 | Deem et al. |
| 8,406,894 B2 | 3/2013 | Johnson et al. |
| 8,469,951 B2 | 6/2013 | Ben-Haim et al. |
| 8,535,302 B2 | 9/2013 | Ben-Haim et al. |
| 8,688,228 B2 | 4/2014 | Johnson et al. |
| 8,825,176 B2 | 9/2014 | Johnson et al. |
| 8,853,600 B2 | 10/2014 | Spertell |
| 8,939,914 B2 | 1/2015 | Turnquist et al. |
| 9,028,477 B2 | 5/2015 | Ben-Haim et al. |
| 9,149,331 B2 | 10/2015 | Deem et al. |
| 9,216,058 B2 | 12/2015 | Spertell |
| 9,241,763 B2 | 1/2016 | Kim et al. |
| 9,314,301 B2 | 4/2016 | Ben-Haim et al. |
| 2001/0005775 A1 | 6/2001 | Samson |
| 2001/0016761 A1 | 8/2001 | Rudie et al. |
| 2001/0050083 A1 | 12/2001 | Marchitto et al. |
| 2002/0062124 A1 | 5/2002 | Keane |
| 2002/0087151 A1 | 7/2002 | Mody et al. |
| 2002/0156471 A1 | 10/2002 | Stern et al. |
| 2002/0165529 A1 | 11/2002 | Danek |
| 2002/0193851 A1 | 12/2002 | Silverman et al. |
| 2003/0004082 A1 | 1/2003 | Masschelein et al. |
| 2003/0120269 A1 | 6/2003 | Bessette et al. |
| 2003/0130575 A1 | 7/2003 | Desai |
| 2003/0130711 A1 | 7/2003 | Pearson et al. |
| 2003/0158566 A1 | 8/2003 | Brett |
| 2003/0212393 A1 | 11/2003 | Knowlton et al. |
| 2003/0216728 A1 | 11/2003 | Stern et al. |
| 2003/0220639 A1 | 11/2003 | Chapelon et al. |
| 2004/0000316 A1 | 1/2004 | Knowlton et al. |
| 2004/0002705 A1 | 1/2004 | Knowlton et al. |
| 2004/0049251 A1 | 3/2004 | Knowlton |
| 2004/0073115 A1 | 4/2004 | Horzewski et al. |
| 2004/0092875 A1 | 5/2004 | Kochamba |
| 2004/0140028 A1 | 7/2004 | Clark et al. |
| 2004/0186535 A1 | 9/2004 | Knowlton |
| 2004/0206365 A1 | 10/2004 | Knowlton |
| 2004/0210214 A1 | 10/2004 | Knowlton |
| 2004/0230260 A1 | 11/2004 | Macfarland et al. |
| 2004/0243182 A1 | 12/2004 | Cohen et al. |
| 2004/0243200 A1 | 12/2004 | Turner et al. |
| 2004/0249426 A1 | 12/2004 | Hoenig et al. |
| 2005/0010271 A1 | 1/2005 | Merchant |
| 2005/0137654 A1 | 6/2005 | Hoenig et al. |
| 2005/0215901 A1 | 9/2005 | Anderson et al. |
| 2005/0215987 A1 | 9/2005 | Slatkine |
| 2005/0251117 A1 | 11/2005 | Anderson et al. |
| 2005/0251120 A1 | 11/2005 | Anderson et al. |
| 2005/0288666 A1 | 12/2005 | Bertolero et al. |
| 2006/0020309 A1 | 1/2006 | Altshuler et al. |
| 2006/0036300 A1 | 2/2006 | Kreindel |
| 2006/0111744 A1 | 5/2006 | Makin et al. |
| 2006/0112698 A1 | 6/2006 | Cazzini et al. |
| 2006/0129209 A1 | 6/2006 | McDaniel |
| 2006/0151485 A1 | 7/2006 | Cronin |
| 2006/0161228 A1 | 7/2006 | Lach |
| 2006/0167498 A1 | 7/2006 | Dilorenzo |
| 2006/0184205 A1 | 8/2006 | Schuler et al. |
| 2006/0189964 A1 | 8/2006 | Anderson et al. |
| 2006/0206110 A1 | 9/2006 | Knowlton et al. |
| 2006/0259102 A1 | 11/2006 | Slatkine |
| 2006/0264926 A1 | 11/2006 | Kochamba |
| 2006/0265034 A1 | 11/2006 | Aknine et al. |
| 2006/0271028 A1 | 11/2006 | Altshuler et al. |
| 2006/0276860 A1 | 12/2006 | Ferren et al. |
| 2007/0010810 A1 | 1/2007 | Kochamba |
| 2007/0016032 A1 | 1/2007 | Aknine |
| 2007/0020355 A1 | 1/2007 | Schlebusch et al. |
| 2007/0049918 A1 | 3/2007 | Van Der Weide et al. |
| 2007/0060989 A1 | 3/2007 | Deem et al. |

(56) References Cited

U.S. PATENT DOCUMENTS

| | | |
|---|---|---|
| 2007/0078290 A1 | 4/2007 | Esenaliev |
| 2007/0078502 A1 | 4/2007 | Weber et al. |
| 2007/0088413 A1 | 4/2007 | Weber et al. |
| 2007/0179482 A1 | 8/2007 | Anderson |
| 2007/0179535 A1 | 8/2007 | Morrissey et al. |
| 2007/0208399 A1* | 9/2007 | Turner .................. A61N 1/403 607/100 |
| 2007/0233226 A1 | 10/2007 | Kochamba et al. |
| 2007/0237620 A1 | 10/2007 | Mohlhoff et al. |
| 2007/0239140 A1 | 10/2007 | Chechelski et al. |
| 2007/0255355 A1 | 11/2007 | Altshuler et al. |
| 2007/0255362 A1 | 11/2007 | Levinson et al. |
| 2007/0265585 A1 | 11/2007 | Joshi et al. |
| 2007/0270925 A1 | 11/2007 | Levinson |
| 2008/0077201 A1 | 3/2008 | Levinson et al. |
| 2008/0077202 A1 | 3/2008 | Levinson |
| 2008/0077211 A1 | 3/2008 | Levinson et al. |
| 2008/0091183 A1 | 4/2008 | Knopp et al. |
| 2008/0119830 A1 | 5/2008 | Ramstad et al. |
| 2008/0154259 A1 | 6/2008 | Gough et al. |
| 2008/0167585 A1 | 7/2008 | Khen et al. |
| 2008/0195000 A1 | 8/2008 | Spooner et al. |
| 2008/0228526 A1 | 9/2008 | Locke et al. |
| 2008/0269851 A1* | 10/2008 | Deem .................. A61B 18/18 607/101 |
| 2008/0294152 A1 | 11/2008 | Altshuler et al. |
| 2008/0319437 A1 | 12/2008 | Turner et al. |
| 2009/0221999 A1 | 9/2009 | Shahidi |
| 2009/0299361 A1 | 12/2009 | Flyash et al. |
| 2009/0299364 A1 | 12/2009 | Batchelor et al. |
| 2009/0306647 A1 | 12/2009 | Leyh et al. |
| 2009/0306659 A1 | 12/2009 | Buysse |
| 2009/0318917 A1 | 12/2009 | Leyh et al. |
| 2010/0010480 A1 | 1/2010 | Mehta et al. |
| 2010/0016782 A1 | 1/2010 | Oblong |
| 2010/0114086 A1 | 5/2010 | Deem et al. |
| 2010/0168727 A1* | 7/2010 | Hancock ............ A61B 18/1815 606/33 |
| 2010/0211059 A1 | 8/2010 | Deem et al. |
| 2011/0015687 A1 | 1/2011 | Nebrigic et al. |
| 2011/0028898 A1 | 2/2011 | Clark, III et al. |
| 2011/0112520 A1 | 5/2011 | Kreindel |
| 2011/0196365 A1 | 8/2011 | Kim et al. |
| 2011/0313412 A1 | 12/2011 | Kim et al. |
| 2012/0078141 A1 | 3/2012 | Knowlton |
| 2012/0265277 A1 | 10/2012 | Unetich |
| 2013/0150844 A1 | 6/2013 | Deem et al. |
| 2014/0180271 A1 | 6/2014 | Johnson et al. |
| 2015/0148792 A1 | 5/2015 | Kim et al. |
| 2015/0351838 A1 | 12/2015 | Deem et al. |
| 2016/0045755 A1 | 2/2016 | Chun et al. |
| 2016/0213426 A1 | 7/2016 | Ben-Haim et al. |
| 2017/0252105 A1 | 9/2017 | Deem et al. |

FOREIGN PATENT DOCUMENTS

| | | |
|---|---|---|
| CN | 1781462 A | 6/2006 |
| EP | 0139607 B1 | 4/1990 |
| EP | 0370890 B1 | 11/1995 |
| EP | 1346753 A2 | 9/2003 |
| JP | 61-364 A | 1/1986 |
| JP | 62-149347 | 9/1987 |
| JP | S-63177856 A | 7/1988 |
| JP | 07-503874 | 4/1995 |
| JP | H09-239040 A | 9/1997 |
| JP | 2001-514921 A | 9/2001 |
| JP | 2006503618 | 2/2006 |
| JP | 2006-289098 | 10/2006 |
| JP | 2007191192 A | 8/2007 |
| JP | 2010524587 A | 7/2010 |
| JP | 54-079994 B2 | 11/2013 |
| WO | WO 89/02292 A1 | 3/1989 |
| WO | WO 92/07622 A1 | 5/1992 |
| WO | WO 96/23447 A1 | 8/1996 |
| WO | WO 96/41579 A1 | 12/1996 |
| WO | WO 99/46005 A1 | 9/1999 |
| WO | WO 00/24463 A2 | 5/2000 |
| WO | WO 01/58361 A1 | 8/2001 |
| WO | WO 03/039385 A2 | 5/2003 |
| WO | WO 2004/034925 A2 | 4/2004 |
| WO | WO 2005/060354 A2 | 7/2005 |
| WO | WO 2005/099369 A2 | 10/2005 |
| WO | WO 2005/112807 A2 | 12/2005 |
| WO | WO 2005/120379 A2 | 12/2005 |
| WO | WO2005/122694 A2 | 12/2005 |
| WO | WO 2006/089227 A2 | 8/2006 |
| WO | WO 2006/090217 A1 | 8/2006 |
| WO | WO 2006/117682 A2 | 11/2006 |
| WO | WO 2006/122136 A2 | 11/2006 |
| WO | WO 2007/015247 A2 | 2/2007 |
| WO | WO 2007/030367 A2 | 3/2007 |
| WO | WO 2007/038567 A1 | 4/2007 |
| WO | WO 2007/050572 A2 | 5/2007 |
| WO | WO2007/093998 A1 | 8/2007 |
| WO | WO 2007/106339 A2 | 9/2007 |
| WO | WO2007/108516 A1 | 9/2007 |
| WO | WO 2007/131112 A2 | 11/2007 |
| WO | WO 2007/140469 A2 | 12/2007 |
| WO | WO2008/068485 A2 | 6/2008 |
| WO | WO 2009/072108 A2 | 6/2009 |
| WO | WO 2011/087852 A2 | 7/2011 |
| WO | WO 2012/072250 A1 | 6/2012 |
| WO | WO2012/138056 A1 | 10/2012 |
| WO | WO2013/074664 A1 | 5/2013 |

OTHER PUBLICATIONS

Deem et al.; U.S. Appl. No. 15/252,109 entitled "Systems and methods for creating an effect using microwave energy to specified tissue," filed Aug. 30, 2016.

Deem et al.; U.S. Pat. Appl. No. 15/288,949 entitled "Methods, devices, and systems for non-invasive delivery of microwave therapy," filed Oct. 7, 2016.

Abraham et al.; Monopolar radiofrequency skin tightening; Facial Plast Surg Clin N Am; 15(2); pp. 169-177; May 2007.

Absar et al.; Efficacy of botulinum toxin type A in the treatment of focal axillary hyperhidrosis; Dermatol Surg; 34(6); pp. 751-755; Jun. 2008.

Acculis; Microwave Ablation for Healthcare Professionals; 2 pgs.; accessed Jun. 24, 2008; (http://www.acculis.com/mta).

Aesthera US—How it Works; 2 pgs.; accessed Jul. 8, 2008 (http://www.aesthera.com/go/aestheralUS/patients/how_it_works/index.cfm).

Allergan Pharmaceuticals; Botox® (product insert); 16 pgs.; Oct. 2006.

Alster et al.; Improvement of neck and cheek laxity with a non-ablative radiofrequency device: a lifting experience; Dermatol Surg; 30(4); pp. 503-507; Apr. 2004.

Ananthanarayanan et al.; 2.5 GHz microwave thermal ablation for performing thermosensitive polymer-chemotherapy for cancer; Antennas and Propagation Society Int. Symp. (APSURSI), 2010 IEEE; Toronto, ON, Canada; pp. 1-4; Jul. 11-17, 2010.

Arneja et al.; Axillary hyperhidrosis: a 5-year review of treatment efficacy and recurrence rates using a new arthroscopic shaver technique; Plast. Reconstr. Surg.; vol. 119; pp. 562-567; Feb. 2007.

Ashby et al.; Cryosurgery for Axillary Hyperhidrosis; British Medical Journal Short Reports; London; pp. 1173-1174; Nov. 13, 1976.

Atkins et al.; Hyperhidrosis: A Review of Current Management; Plast Reconstr Surg; 110(1); pp. 222-228; Jul. 2002.

Avedro; Keraflex KXL—A new treatment option in European clinical trials; 1 pg.; Sep. 2009; printed Jun. 18, 2012 from website (http://www.nkcf.org/research/research-update/139-kxl-clinical-trials.html).

Ball, P.; Radio sweat gland—90 GHz; Nature; 452(7188); p. 676; Apr. 9, 2008; printed Jun. 18, 2012 from website (http://www.nature.com/news/2008/080409/full/452676a.html).

Basra et al.; The dermatology life quality index 1994R2007: A comprehensive review of validation data and clinical results; Br J Dermatol;159(5); pp. 997-1035; Nov. 2008.

(56) References Cited

OTHER PUBLICATIONS

Bechara et al.; Histological and clinical findings in different surgical strategies for focal axillary hyperhidrosis; Dermatol Surg; vol. 34; pp. 1001-1009; Aug. 2008.

Beer et al., Immunohistochemical Differentiation and Localization Analysis of Sweat Glands in the Adult Human Axilla, Plastic and Reconstructive Surgery, vol. 117, No. 6, pp. 2043-2049, May 2006.

Bentel et al.; Variability of the depth of supraclavicular and axillary lymph nodes in patients with breast cancer: is a posterior axillary boost field necessary?; Int J Radiation Oncology Biol Phys; vol. 47(3); pp. 755-758; Jun. 2000.

Bindu et al.; Microwave characterization of breast-phantom materials; Microwave and Optical Tech. Letters; 43(6); pp. 506-508; Dec. 20, 2004.

Bioportfolio; Tenex Health Receives FDA clearance for innovative TX1} tissue removal system; 2 pgs.; release dated Mar. 9, 2011; printed on Jun. 18, 2012 from website (http://www.bioportfolio.com/news/article/519143/Tenex-Health-Receives-Fda-Clearance-For-Innovative-Tx1-Tissue-Removal-System.html).

Blanchard et al.; Relapse and morbidity in patients undergoing sentinel lymph node biopsy alone or with axillary dissection for breast cancer; Arch Surg; vol. 138; pp. 482-488; May 2003.

Brace et al., Microwave Ablation with a Trixial Antenna: Results in ex vivo Bovine Liver, IEEE transactions on Microwave Theory and Techniques, vol. 53, No. 1, pp. 215-220 (Jan. 2005).

BSD Medical Corporation; Hyperthermia therapy contributes to 85 percent survival rate from childhood cancers; 2 pgs.; Jan. 13, 2009; printed Jun. 18, 2009 from website (http://www.irconnect.com/noc/press/pages/news_releases.html?d=157551).

Bu-Lin et al.; A polyacrylamide gel phantom for radiofrequency ablation; Int. J. Hyperthermia; 24(7); pp. 568-576; Nov. 2008.

Burns, Jay A.; Thermage: monopolar radiofrequency; Aesthetic Surg J; 25(6); pp. 638-642; Nov./Dec. 2005.

Business Wire; miraDry by Miramar Labs Receives FDA 510(k) Clearance; 2pgs.; Feb. 8, 2011; printed Jun. 18, 2012 from website (http://www.businesswire.com/news/home/20110208005595/en/miraDry-Miramar-Labs-Receives-FDA-510-Clearance).

Campbell et al.; Dielectric properties of female human breast tissue measured in vitro at 3.2 GHz; Phys. Med. Biol.; 37(1); pp. 193-210; Jan. 1992.

Candela Corp.; The Candela SeleroPLUS Laser with Dynamic Cooling Device: The Benefits of Anesthesia without the Risks; Nov. 1998.

Chang et al.; A conductive plastic for simulating biological tissue at microwave frequencies; IEEE Trans on Electromagnetic Compatibility; 42(1); pp. 76-81; Feb. 2000.

Christ et al., Characterization of the Electromagnetic Near-Field Absorption in Layered Biological Tissue in the Frequency Range from 30 MHz to 6000 MHz, Phys. Med. Biol. 51, pp. 4951-4965; Oct. 2006.

Christ et al., The Dependence of Electromagnetic Far-Field Absorption on Body Tissue Composition in the Frequency Range from 300 MHz to 6 GHz, IEEE Transactions on Microwave Theory and Techniques, vol. 54, No. 5, pp. 2188-2195 (May 2006).

CK Electronic GmbH; Scientific Measurements of Skin and Hair (product information); 15 pgs.; published after Sep. 2006.

Cobham; Antenna & Radome Design Aids (product list); 1 pg.; Aug. 2001.

Commons et al.; Treatment of axillary hyperhidrosis/bromidrosis using VASER ultrasound; Aesth Plast Surg; vol. 33(3); pp. 312-323; May 2009 (pub'd online Jan. 3, 2009).

Copty et al., Low-power near-field microwave applicator for localized heating of soft matter, Applied Physics Letters, vol. 84, No. 25, pp. 5109-5111 (Jun. 21, 2004).

Covidien; FDA clears Covidien's Evident} microwave ablation system for use in nonresectable liver tumor ablation; 2 pgs.; Dec. 28, 2008; printed Jun. 18, 2012 from website (http://www.medicalnewstoday.com/releases/133800.php).

Darabaneanu et al.; Long-term efficacy of subcutaneous sweat gland suction curettage for axillary hyperhidrosis: a prospective gravimetrically controlled study; Dermatol Surg; 34(9); pp. 1170-1177; Sep. 2008.

De Bruijne et al., Effects of waterbolus size, shape and configuration on the SAR distribution pattern of the Lucite cone applicator, International Journal of Hyperthermia, 22(1): 15-28 (Feb. 2006).

Dewey; Arrhenius relationships from the molecule and cell to the clinic; Int. J. Hyperthermia; 25(1); pp. 3-20; Feb. 2009.

Diederich et al.; Pre-clinical Evaluation of a Microwave Planar Array Applicator for Superficial Hyperthermia; International Journal of Hyperthermia; vol. 9, No. 2; pp. 227-246; Jan. 1993.

Drozd et al.; Comparison of Coaxial Dipole Antennas for Applications in the Near-Field and Far-Field Regions; MW Journal, vol. 47, No. 5 (May 2004), http://www.mwjournal.com/Journal, accessed Dec. 10, 2007.

Duparc et al.; Anatomical basis of the variable aspects of injuries of the axillary nerve (excluding the terminal branches in the deltoid muscle); Surg Radiol Anat; vol. 19(3); pp. 127-132; May 1997.

Eleiwa et al.; Accurate FDTD simulation of biological tissues for bio-electromagnetic applications; IEEE Proc. SoutheastCon 2001; Clemson, SC; Mar. 30-Apr. 1, 2001; pp. 174-178.

Farace et al.; An automated method for mapping human tissue permittivities by MRI in hyperthermia treatment planning; Phys. Med. Biol.; 42(11); pp. 2159-2174; Nov. 1997.

Fitzpatrick et al.; Multicenter study of noninvasive radiofrequency for periorbital tissue tightening; Lasers Sur Med; 33(4); pp. 232-242; Mar. 2003.

Gabriel et al.; Dielectric parameters relevant to microwave dielectric heating; Chem Soc Rev; 27(3); pp. 213-224; May-Jun. 1998.

Gabriel et al.; The dielectric properties of biological tissues: I. Literature survey; Phys Med Biol; 41(11); pp. 2231-2249; Nov. 1996.

Gabriel et al.; The dielectric properties of biological tissues: II. Measurements in the frequency range 10 Hz to 20 GHz; Phys Med Biol; 41(11); pp. 2251-2269; Nov. 1996.

Gabriel et al.; The dielectric properties of biological tissues: III. Parametric models for the dielectric spectrum of tissues; Phys Med Biol; 41(11); pp. 2271-2293; Nov. 1996.

Gabriel, et al.; Comparison of the Dielectric Properties of Normal and Wounded Human Skin Material; Bioelectromagnetics; 8; pp. 23-27; Jan. 1987.

Gabriel; Compilation of the dielectric properties of body tissues at Rf and microwave frequencies (Technical Report); Armstrong Laboratory; Doc. No. AL/OE-TR-1996-004; pp. 1-16; Jan. 1996.

Galloway et al.; Ultrasound imaging of the axillary vein—anatomical basis for central venous access; British ournal of Anaesthesia; 90(5); pp. 589-595; May 2003.

Gandhi et al.; Electromagnetic Absorption in the Human Head and Neck for Mobile Telephones at 835 and 1900 MHz; IEEE Transactions on Microwave Theory and Techniques; 44(10); pp. 1884-1897; Oct. 1996.

Gandhi et al.; Electromagnetic Absorption in the Human Head from Experimental 6-GHz Handheld Transceivers; IEEE Trans. on Electromagnetic Compatibility; 37(4); pp. 547-558; Nov. 1995.

Garber, B. B.; Office microwave treatment of enlarged prostate symptoms; 2 pgs.; printed from website (http://www.garber-online.com/microwave-treatment.htm) on Jun. 18, 2012.

Glaser et al.; A randomized, blinded clinical evaluation of a novel microwave device for treating axillary hyperhidrosis: the dermatologic reduction in underarm perspiration study; Dermatol Surg; 38(2); pp. 185-191; Feb. 2012.

Glaser et al.; A randomized, blinded clinical evaluation of a novel microwave device for treatinment of axillary hyperhidrosis; 2010 ASDS/ASCDAS Joint Annual Meeting; Late Breaking Abstract (GD413); Oct. 2010.

Gold et al.; Treatment of Wrinkles and Skin Tightening Using Aluma(TM) Skin Renewal System with Faces(TM)(Functional Aspiration Controlled Electrothermal Stimulation) Technology; Lumens, Inc. (Oct. 2005).

Goldman et al.; Subdermal Nd—Yag laser for axillary hyperhidrosis; Dermatol Surg; 34(6); pp. 756-762; Jun. 2008.

(56) References Cited

OTHER PUBLICATIONS

Guidant Corp.; Guidant microwave surgical ablation system; 1 pg.; © 2004; printed Jun. 18, 2012 from website (http://web.archive.org/web/20070306031424/http://www.ctsnet.org/file/vendors/872/Pdf/MicrowaveAblationIFU.pdf).
Guy, Arthur; History of Biological Effects and Medical Applications of Microwave Energy; IEEE Transactions on Microwave Theory and Techniques; 32(9); pp. 1182-1200; Sep. 1984.
Guy, Arthur; Therapeutic Heat and Cold, Fourth Ed.; Chapter 5: Biophysics of High-Frequency Currents and Electromagnetic Radiation; pp. 179-236. Williams and Wilkins (publishers); Apr. 1990.
Guy; Analyses of electromagnetic fields induced in biological tissues by thermographic studies on equivalent phantom models; IEEE Trans on Microwave Theory and Techniques; MTT-19(2); pp. 205-214; Feb. 1971.
Haedersdal et al.; Evidence-based review of hair removal using lasers and light sources; JEADV; vol. 20; pp. 9-20; Jan. 2006.
Hey-Shipton, et al.; The Complex Permittivity of Human Tissue at Microwave Frequencies; Phys. Med. Biol.; 27(8); pp. 1067-1071; Aug. 1982.
Hisada et al.; Hereditary Hemorrhagic Telangiectasia Showing Severe Anemia which was successfully treated with estrogen; International Medicine; vol. 34; No. 6; pp. 589-592; Jun. 1995.
Hodgkinson, D. J.; Clinical applications of radiofrequency: nonsurgical skin tightening (thermage); Clin Plastic Surg; 36(2); pp. 261-268; Apr. 2009.
Hong et al.; Clinical evaluation of a microwave device for treating axillary hyperdrosis; Dermatol Sug; 38(5); pp. 728-735; May 2012.
Hornberger et al.; Recognition, diagnosis, and treatment of primary focal hyperhidrosis; J Am Acad Dermatol; vol. 51; pp. 274-286; Aug. 2004.
Houzen et al.; Implanted antenna for an artificial cardiac pacemaker system; Progress in Electromagnetics Research Symposium 2007; Prague, CZ; pp. 51-54; Aug. 27-30, 2007.
Hu, Da Zhang, Electromagnetic Field in Organism of Skin-Fat-Muscle, China Research Institute of Radiowave Propagation IEEE, pp. 807-812 (Aug. 1998).
Jacob, Carolyn,Treatment of Hyperhidrosis with Microwave Technology, Semin Cutan Med Surg; 32(8); pp. 2-8; Mar. 2013.
Jacobsen et al.; Characteristics of microstrip muscle-loaded single-arm archimedean spiral antennas as investigated by FDTD numerical computations; IEEE Trans. on Biomedical Engineering; 52(2); pp. 321-330; Feb. 2005.
Jacobsen et al.; Characterization of a tranceiving antenna concept for microwave heating and thermometry of superficial tumors; Pier; vol. 18; pp. 105-125; (year of publication is sufficiently earlier than the effective U.S. filing date and any foreign priority date) 1998.
Jacobsen et al.; Dual-mode antenna design for microwave heating and noninvasive thermometry of superficial tissue disease; IEEE Trans. on Biomedical Engineering; 47(11); pp. 1500-1509; Nov. 2000.
Jacobsen et al.; Multifrequency radiometric determination of temperature profiles in a lossy homogeneous phantom using a dual-mode antenna with integral water bolus; IEEE Trans. on Microwave Theory and Techniques; 50(7); pp. 1737-1746; Jul. 2002.
Jacobsen et al.; Nonparametric 1-D temperature restoration in lossy media using tikhonov regularization on sparse radiometry data; IEEE Trans. on Biomedical Engineering; 50(2); pp. 178-188; Feb. 2003.
Jacobsen et al.; Transceiving antenna for homogenious heating and radiometric thermometry during hyperthermia; Electronic Letters; 36(6); pp. 496-497; Mar. 16, 2000.
Johnson et al.; Automatic temperature controller for multielement array hyperthermia systems; IEEE Trans. on Biomedical Engineering; 53(6); pp. 1006-1015; Jun. 2006.
Johnson et al.; Evaluation of a dual-arm Archimedean spiral array for microwave hyperthermia; Int J Hyperthermia; 22(6); pp. 475-490; Sep. 2006.
Johnson et al.; Microwave thermolysis of sweat glands; Lasers in Surgery and Medicine; 44(1); pp. 20-25; Jan. 2012.
Juang et al.; Construction of a conformal water bolus vest applicator for hyperthermia treatment of superficial skin cancer; Proc. of the 26th Ann. Int. Conf. of the IEEE EMBS; San Francisco, CA, USA; Sep. 1-5, 2004; pp. 3467-3470.
Kaminer et al.; First clinical use of a novel microwave device for treatment of axillary hyperhidrosis; 2010 ASDS Annual Meeting; Poster #12; Oct. 2010.
Kawoos et al., Issues in Wireless Intracranial Pressure Monitoring at Microwave Frequencies, PIERS Online, vol. 3, No. 6, pp. 927-931; 2007 (year of publication is sufficiently earlier than the effective U.S. filing date and any foreign priority date).
Kilmer et al.; A randomized, blinded clinical study of a microwave device for treatment of axillary hyperhidrosis; 31st ASLMS Annual Conference; Late-Breaking Abstract; Apr. 1-3, 2011.
Kim et al.; Implanted antennas inside a human body: Simulations, designs, and characterizations; IEEE Trans on Microwave Theory and Techniques; 52(8); pp. 1934-1943; Aug. 2004.
Kirn, T. F.; Researchers seek to quantify thermage efficacy; Dermatologic Surgery; p. 36; Jan. 2007.
Kirsch et al.; Ultrastructure of collagen thermally denatured by microsecond domain pulsed carbon dioxide laser; Arch Dermatol; 134; pp. 1255-1259; Oct. 1998.
Klemm et al.; EM energy absorption in the human body tissues due to UWB antennas; Progress in Electromagnetics Research; PIER; 62; pp. 261-280; (year of pub. sufficiently earlier than effective US filing date and any foreign priority date) 2006.
Kobayashi, T.; Electrosurgery Using Insulated Needles: Treatment of Axillary Bromhidrosis and Hyperhidrosis; Journal of Dermatologic Surgery & Oncology; 14(7) pp. 749-752; Jul. 1988.
Krusen, Frank (M.D.); Samuel Hyde Memorial Lecture: Medical Applications of Microwave Diathermy: Laboratory and Clinical Studies. Proceedings of the Royal Society of Medicine; 43(8); pp. 641-658, May 10, 1950.
Kumaradas et al.; Optimization of a beam shaping bolus for superficial microwave hyperthermia waveguide applicators using a finite element method; Phys. Med. Biol.; 48(1); pp. 1-18; Jan. 7, 2003.
Kushikata, Nobuharu, Histological Assessment of Biopsy Samples Taken Before and After the mireDry Procedure Performed on a Patient with Axillary Hyperhidrosis; Case Report; pp. 1-3; Oct. 2011.
Lagendijk et al; Hyperthermia dough: a fat and bone equivalent phantom to test microwave/radiofrequency hyperthermia heating systems; Phys. Med. Biol.; 30(7); pp. 709-712; Jul. 1985.
Land et al.; A quick accurate method for measuring the microwave dielectric properties of small tissue samples; Phys. Med. Biol.; 37(1); pp. 183-192; Jan. 1992.
Lane et al.; Pressure-Induced Bullae and Sweat Gland Necrosis Following Chemotherapy Induction; the American Journal of Medicine; vol. 117; pp. 441-443; Sep. 15, 2004.
Larson et al.; Microwave treatments for enlarged prostate cause blood pressure surges, study shows; 2 pgs.; Apr. 11, 2008; printed on Jun. 18, 2012 from website (http://web.archive.org/web/20080415000815/http://www.sciencedaily.com/releases/2008/04/080408105820.htm).
Lawrence et al.; Selective Sweat Gland Removal with Minimal Skin Excision in the Treatment of Axillary Hyperhidrosis: A Retrospective Clinical and Histological Review of 15 Patients; British Journal of Dermatology; British Association of Dermatologists; 155(1), pp. 115-118; Jul. 2006.
Lehmann et al.; Therapeutic Heat; Therapeutic Heat and Cold, Fourth Ed.; Chapter 9; pp. 417-581; Williams & Wilkins (publishers), Baltimore, MD; Apr. 1990.
Lowe et al.; Botulinum toxin type a in the treatment of primary axillary hyperhidrosis: A 52-week multicenter double-blind, randomized, placebo-controlled study of efficacy and safety; J Am Acad Dermatol; vol. 56; pp. 604-611; Apr. 2007.
Lowe et al.; Microwave delivery system for lower leg telangiectasia; Journal of Cutaneous Laser Therapy; 2(1); pp. 3-7; Mar. 2000.
Lumenis Inc.; Aluma RF Skin Renewal System (product information); copyright 2007 (PB-1013670); 8 pgs.; Oct. 2007 (printed version).

(56) References Cited

OTHER PUBLICATIONS

Lupin et al.; A Multi-Center Evaluation of the miraDry System to Treat Subjects with Axillary Hyperhidrosis; 31st ASLMS Annual Conference; Abstract # 79; Apr. 1-3, 2011.

Lupin et al.; Long-term evaluation of microwave treatment for axillary hyperhidrosis; 2012 ASLMS Annual Meeting; pp. 6-7; Abstract #19; Apr. 2012.

Lupin et al.; Microwave-based treatment for primary axillary hyperhidrosis: Six months of follow-up; J Am Acad Dermatol; 66(4), supp. 1; p. AB215; Poster #5300; Apr. 2012.

MacCarini et al.; Advances in microwave hyperthermia of large superficial tumors; Microwave Symposium Digest, IEEE MTT-S International; pp. 1797-1800; Jun. 2005.

MacCarini et al.; Electromagnetic optimization of dual mode antennas for radiometry controlled heating of superficial tissue; Proceedings of SPIE; vol. 5698; Bellingham, WA; pp. 71-81; Jan. 2005.

MacCarini et al.; Optimization of a dual concentric conductor antenna for superficial hyperthermia applications; Proc. of the 26th Ann. Int. Conf. of the IEEE EMBS; San Francisco, CA, USA; Sep. 1-5, 2004; pp. 2518-2521.

Mazzurana et al.; A semi-automatic method for developing an anthropomorphic numerical model of dielectric anatomy by MRI; Phys. Med. Biol.; 48(19); pp. 3157-3170; Oct. 7, 2003.

MedGadget; MedGadget's MedTech Monday: Treating excessive underarm sweat with microwaves; 1 pg.; Feb. 14, 2011; printed Jun. 18, 2012 from website (https://www.massdevice.com/blogs/massdevice/medgadgets-medtech-monday-treating-excessive-underarm-sweat-with-microwaves).

MedWaves, Inc.; MedWaves, Inc. sponsors investigational studies to evaluate its patented microwave thermal coagulation-ablation system for treatment of tumors in liver and lung; 4 pgs.; Sep. 18, 2009; printed Jun. 18, 2012 from website (http://www.ereleases.com/pr/medwaves-sponsors-investigational-studies-evaluate-patented-microwave-thermal-coagulationablation-system-treatment-tumors-liver-lung-25870).

Michel et al.; Design and Modeling of Microstrip-Microslot Applicators with Several Patches and Apertures for Microwave Hyperthermia; Microwave and Optical Technology Letters; vol. 14, No. 2; pp. 121-125; Feb. 5, 1997.

Mrozowski et al.; Parameterization of media dispersive properties for FDTD; IEEE Trans on Antennas and Propagation; 45(9); pp. 1438-1439; Sep. 1997.

Nagaoka et al.; Development of realistic high-resolution whole-body voxel models of Japanese adult males and females of average height and weight, and application of models to radio-frequency electromagnetic-field dosimetry; Phys. Med. Biol.; 49(1); pp. 1-15; Jan. 7, 2004.

Neuman; SAR pattern perturbations from resonance effects in water bolus layers used with superficial microwave hyperthermia applicators; Int. J. Hyperthermia; 18(3); pp. 180-193; May-Jun. 2002.

Park et al.; A Comparative Study of the Surgical Treatment of Axillary Osmidrosis by Instrument, Manual, and Combined Subcutaneous Shaving Procedures; 41(5); pp. 488-497; Nov. 1998.

Paulides et al.; A Patch Antenna Design for Application in a Phased-Array Head and Neck Hyperthermia Applicator; IEEE Transactions on Biomedical Engineering; 54(11); pp. 2057-2063; Nov. 2007.

Peyman et al.; Cole-cole parameters for the dielectric properties of porcine tissues as a function of age at microwave frequencies; Phys Med Biol; 55(15); pp. N413RN419; Jul. 2010.

Popovic et al.; Dielectric spectroscopy of breast tissue-improved model of the precision open-ended coaxial probe; Proc of the 25th Ann Int Conf of the IEEE EMBS; Cancun, Mexico; pp. 3791-3793; Sep. 17-21, 2003.

Popovic et al.; Response characterization of the precision open-ended coaxial probe for dielectric spectroscopy of breast tissue; 2003 IEEE—Anntennas and Propagation Soc. Int. Symp.; vol. 4; pp. 54-57; Jun. 22-27, 2003.

Pozar, David M.; Electromagnetic Theory (Introduction); Microwave Engineering, Second Edition; John Wiley & Sons, Inc.; p. 1; Aug. 1997.

Rappaport, C.; Treating Cardiac Disease with Catheter-Based Tissue Heating; IEEE Microwave Magazine; 3(1); pp. 57-64; Mar. 2002.

Riddle et al.; Complex permittivity measurements of common plastics over variable temperatures; IEEE Trans on Microwave Theory and Techniques; vol. 51(3); pp. 727-733; Mar. 2003.

Rolfsnes et al.; Design of spiral antennas for radiometric temperature measurement; Proc. of the 26th Ann. Int. Conf. of the IEEE EMBS; San Francisco, CA, USA; Sep. 1-5, 2004; pp. 2522-2525.

Rosen et al.; Microwaves treat heart disease; IEEE Microw Mag; 8(1); pp. 70-75; Feb. 2007.

Ross et al.; A pilot study of in vivo immediate tissue contraction with CO2 skin laser resurfacing in a live farm pig; Dermatol Surg; 25(11); pp. 851-856; Nov. 1999.

Ross et al.; Comparison of carbon dioxide laser, erbium: Yag laser, dermabrasion, and dermatome A study of thermal damage, wound contraction, and woundhealing in a live pig model: Implications for skin. resurfacing; J Am Acad Dermatol; 42(1); pp. 92-105; Jan. 2000.

Ross et al.; Use of a novel erbium laser in a yucatan minipig: A study of residual thermal damage, ablation, and wound healing as a function of pulse duration; Lasers Surg Med; 30(2); pp. 93-100; Feb. 2002.

Rossetto et al.; Effect of complex bolus-tissue load configurations on SAR distributions from dual concentric conductor applicators; IEEE Trans. on Biomedical Engineering; 46(11); pp. 1310-1319; Nov. 1999.

Saito et al.; Clinical Trials of Interstitual Microwave Hyperthermia by Use of Coaxial-Slot Antenna With Two Slots; IEEE Trans. on Microwave Theory and Techniques; vol. 52; No. 8; pp. 1987-1991; Aug. 2004.

Sherar et al.; Helical antenna arrays for interstitial microwave thermal therapy for prostate cancer: tissue phantom testing and simulations for treatment; Physics in Medicine and Biology; 46(7); pp. 1905-1918; Jul. 2001.

Shimm, D et al.; Hyperthermia in the Treatment of Malignancies; Therapeutic Heat and Cold Fourth Edition edited by Justin Lehmann M.D., Chapter 14, pp. 674-699, Williams & Wilkins Publishers, Baltimore, MD; Apr. 1990.

Sipahioglu et al.; Dielectric properties of vegetables and fruits as a function of temperature, ash, and moisture content; Journal of Food Science; 68(1); pp. 234-239; Jan. 2003.

Smith, Stacy; Evolution of a new treatment modality for primary focal hyperhidrosis(poster); Cosmetic Boot Camp 2011; Aspen, CO; Jul. 2011.

Solish et al.; A comprehensive approach to the recognition, diagnosis, and severity-based treatment of focal hyperhidrosis: recommendations of the Canadian hyperhidrosis advisory committee; Dermatol Surg; vol. 33; pp. 908-923; Aug. 2007.

Solish et al.; Prospective open-label study of botulinum toxin type a in patients with axillary hyperhodrosis: effects on functional impairment and quality of life; Dermatol Surg; vol. 31(4); pp. 405-413; Apr. 2005.

Solta Medical, Inc.; Study Published in Facial Plastic Surgery Journal Finds Selective Heating of Fibrous Septae Key to Success and Safety of Thermage(R) ThermaCool(TM) System; Thermage® Press Release; 2 pgs.; Jun. 20, 2005.

Soontornpipit et al.; Design of implantable microstrip antenna for communication with medical implants; IEEE Trans on Microwave Theory and Techniques; 52(8); pp. 1944-1951; Aug. 2004.

Spertell et al.; Review of clinical data on hair removal using the MW 2000 microwave delivery system (promotional material); 2000; MW Medical, Inc.; printed from http://www.hairfacts.com/medpubs/mwave/spertell.html on Jun. 23, 2009; 5 pgs.

Spertell; Presentation at the American Academy of Dermatology; MW Medical, Inc.; Mar. 10, 2000; 21 pgs.

Spertell; The application of microwaves to the treatment of cosmetic skin conditions: a technical summary; MW Medical, Inc.; pp. 1-15; May 25, 1999.

(56) References Cited

OTHER PUBLICATIONS

Srli Technologies; BTC-2000} (product information); printed from website: http://www.srli.com/technologies/BTC2000.html on Nov. 16, 2009; 1 pg.

Stauffer et al.; Combination applicator for simultaneous heat and radiation; Proc. of the 26th Ann. Int. Conf. of the IEEE EMBS; San Francisco, CA, USA; Sep. 1-5, 2004; pp. 2514-2517.

Stauffer et al.; Dual mode antenna array for microwave heating and non-invasive thermometry of superficial tissue disease; SPIE Conf. on Thermal Treatment of Tissue with Image Guidance; San Jose, CA; SPIE; vol. 3594; pp. 139-147; Jan. 1999.

Stauffer et al.; Microwave array applicator for rediometry controlled superficial hyperthermia; Proc. of the SPIE; vol. 4247; pp. 19-29; Jun. 2001.

Stauffer et al.; Phantom and animal tissues for modelling the electrical properties of human liver; Int. J. Hyperthermia; 19(1); pp. 89-101; Jan.-Feb. 2003.

Stauffer et al.; Practical induction heating coil designs for clinical hyperthermia with ferromagnetic implants; IEEE Trans. on Biomedical Engineering; 41(1); pp. 17-28; Jan. 1994.

Stauffer et al.; Progress on system for applying simultaneous heat and brachytherapy to large-area surface disease; Proceedings of SPIE; vol. 5698; Bellingham, WA; pp. 82-96; Jan. 2005.

Stauffer et al.; Progress toward radiometry controlled conformal microwave array hyperthermia applicator; Proc. of the 22nd Ann. EMBS Int. Conf.; Chicago, IL; Jul. 23-28, 2000; pp. 1613-1616.

Stauffer, Paul R.; Evolving technology for thermal therapy of cancer; International Journal of Hyperthermia; 21(8); pp. 731-744; Dec. 2005.

Stauffer, Paul R.; Thermal Therapy Techniques for Skin and Superficial Tissue Disease; Critical Reviews; SPIE Optical Engineering Press (Bellingham, WA); vol. CR75; pp. 327-367; Jan. 2000.

Sterzer, Fred, Microwave Medical Devices; IEEE Microwave Magazine, 3(1); pp. 65-70; Mar. 2002.

Stoy et al.; Dielectric properties of mammalian tissues from 0.1 to 100 MHz: a summary of recent data; Phys. Med. Bil.; 27(4); pp. 501-513; Apr. 1982.

Strutton et al.; US prevalence of hyperhidrosis and impact on individuals with axillary hyperhidrosis: Results from a national survey. J Am Acad Dermatol; 51(2); pp. 241-248; Feb. 2004.

Stuchly et al.; Diathermy applicators with circular aperture and corrugated flange; IEEE Trans on Microwave Theory and Techniques; MTT-28(3); pp. 267-271; Mar. 1980.

Stuchly et al.; Dielectric properties of animal tissues in vivo at frequencies 10 MHz-1 GHz; Bioelectromagnetics; 2(2); pp. 93-103; Apr. 1981.

Stuchly et al.; Dielectric properties of animal tissues in vivo at radio and microwave frequencies: comparison between species; Phys. Med. Biol.; 27(7); pp. 927-936; Jul. 1982.

Sullivan et al.; Comparison of measured and simulated data in an annular phased array using an inhomogeneous phantom; IEEE Trans on Microwave Theory and Techniques; 40(3); pp. 600-604; Mar. 1992.

Sullivan et al.; The pig as a model for human wound healing; Wound Repair Regen; 9(2); pp. 66-76; Mar. 2001.

Sunaga et al.; Development of a dielectric equivalent gel for better impedance matching for human skin; Bioelectromagnetics; 24; pp. 214-217; Apr. 2003.

Surowiec et al.; Dielectric properties of breast carcinoma ind the surrounding tissues; IEEE Trans on Biomedical Engineering; 35(4); pp. 257-263; Apr. 1988.

Tavernier et al.; Conductivity and dielectric permittivity of dermis and epidermis in nutrient liquid saturation; Engineering in Medicine and Biology Society; 1992 14th Annual Int. Conf of the IEEE; Paris, France; pp. 274-275; Oct. 29-Nov. 1, 1992.

Thermolase Corp.; 510K Pre-Market Notification (No. K950019) and Product User Manual ThermoLase Model LT100 Q-Switched Nd: YAG, Laser Hair Removal System, Jan. 3, 1995.

Trembly et al.; Combined Microwave Heating and Surface Cooling of the Cornea; IEEE Transactions on Biomedical Engineering; vol. 38; No. 1; pp. 85-91; Jan. 1991.

Urolgix, Inc.; Cooled Thermotherapy + Prostiva RF = Durability + Versatility; 1 pg.; printed Jun. 18, 2012 from website (http://www.urologix.com/).

Uzunoglu et al.; A 432-MHz Local Hyperthermia System Using an Indirectly Cooled, Water-Loaded Waveguide Applicator; IEEE Trans. on Microwave Theory and Techniques; vol. 35, No. 2; pp. 106-111; Feb. 1987.

Valleylab; Cool-tip} RF Ablation System; (http://www.cool-tiprf.com/physics.html) accessed Jun. 24, 2008.

Van Rhoon et al.; A 433 MHz Lucite Cone Waveguide Applicator for Superficial Hyperthermia; International Journal of Hyperthermia; vol. 14, No. 1; pp. 13-27; Jan.-Feb. 1998.

Vander Vorst et al.; RF/microwave interaction with biological tissues; Hoboken, NJ; John Wiley & Sons, Inc.; pp. 264-305; Jan. 2006.

Vardaxis et al.; Confocal laser scanning microscopy of porcine skin: Implications for human wound healing studies; J Anat; 190(04); pp. 601-611; May 1997.

Virga et al.; Low-profile enhanced-bandwidth PIFA antennas for wireless communications packaging; IEEE Trans on Microwave Theory and Techniques; 45(10); pp. 1879-1888; Oct. 1997.

Vrba, et al.; Evanescent-Mode Applicators (EMA) for Superficial and Subcutaneous Hyperthermia; IEEE Trans. on Biomedical Engineering; vol. 40; No. 5; pp. 397-407; May 1993.

Warty et al.; Characterization of implantable antennas for intracranial pressure monitoring: reflection by and transmission through a scalp phantom; IEEE Trans on Mircrowave Theory and Techniques; 56(10); pp. 2366-2376; Oct. 2008.

Weiss et al.; Monopolar radiofrequency facial tightening: a retrospective analysis of efficacy and safety in over 600 treatments; J Drugs Dermatol; 5(8); pp. 707-712; Sep. 2006.

Wikipedia; Bayonet mount; 6 pages; Dec. 18, 2014; retrieved from the Internet (www.http://en.wikipedia.org/wiki/Bayonet mount).

Wikipedia; ISM band; 5 pages; printed Jul. 22, 2014 from website (http://en.wikipedia.org/wiki/ISM_band).

Wollina et al.; Tumescent suction curettage versus minimal skin resection with subcutaneous curettage of sweat glands in axillary hyperhidrosis; Dermatol Surg; 34(5); pp. 709-716; May 2008.

Wong, G.; miraDry system: technology to help treat excessive underarm sweat; 1 pg.; Feb. 10, 2011; printed on Jun. 18, 2012 from website (http://www.ubergizmo.com/2011/02/miradry-system-treat-excessive-underarm-sweat/).

Wonnell et al.; Evaluation of microwave and radio frequency catheter ablation in a myocardium-equivalent phantom model; IEEE Trans. on Biomedical engineering; 39(10); pp. 1086-1095; Oct. 1992.

Wright et al.; Hepatic microwave ablation with multiple antennae results in synergistically larger zones of coagulation necrosis; Ann. Surg. Oncol.; 10(3); pp. 275-283; Apr. 2003.

Yang et al.; A Floating Sleeve Antenna Yields Localized Hepatic Microwave Ablation; IEEE Transactions on Biomedical Engineering; 53(3); pp. 533-537; Mar. 2006.

Zelickson et al.; Histological and ultrastructural evaluation of the effects of a radiofrequency-based nonablative dermal remodeling device; Arch Dermatol; 140; pp. 204-209; Feb. 2004.

Zelickson et al.; Ultrastructural effects of an infrared handpiece on forehead and abdominal skin; Dermatol Surg; 32(7); pp. 897-901; Jul. 2006.

Zhou et al.; Resection of Meningiomas with Implantable Microwave Coagualation; Bioelectromagnetics; vol. 17; No. 2; pp. 85-88; (year of publication is sufficiently earlier than the effective U.S. filing date and any foreign priority date) 1996.

Kim et al.; U.S. Appl. No. 15/005,892 entitled "Systems, apparatus, methods and procedures for the noninvasive treatment of tissue using microwave energy," filed Jan. 25, 2016.

Johnson et al.; U.S. Appl. No. 15/667,461 entitled "Systems, apparatus, methods and procedures for the non-invasive treatment of tissue using microwave energy," filed Aug. 2, 2017.

(56) References Cited

OTHER PUBLICATIONS

Deem et al.; U.S. Appl. No. 16/237,494 entitled "Systems and methods for creating an effect using microwave energy to specified tissue," filed Dec. 31, 2018.

Deem et al.; U.S. Appl. No. 15/406,496 entitled "Systems and methods for creating an effect using microwave energy to specified tissue," filed Jan. 13, 2017.

Ben-Haim et al.; U.S. Appl. No. 16/444,831 entitled "Applicator and tissue interface module for dermatological device," filed Jun. 18, 2019.

\* cited by examiner

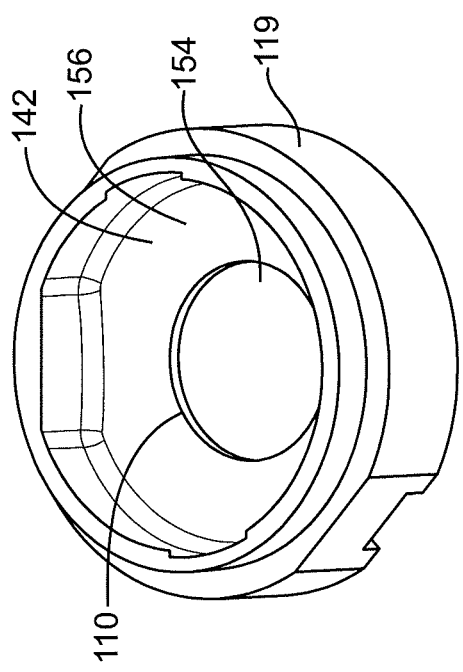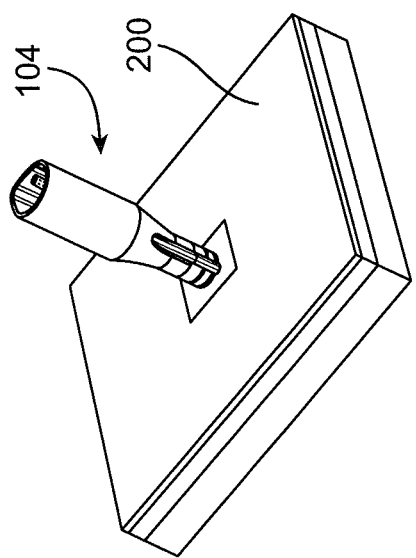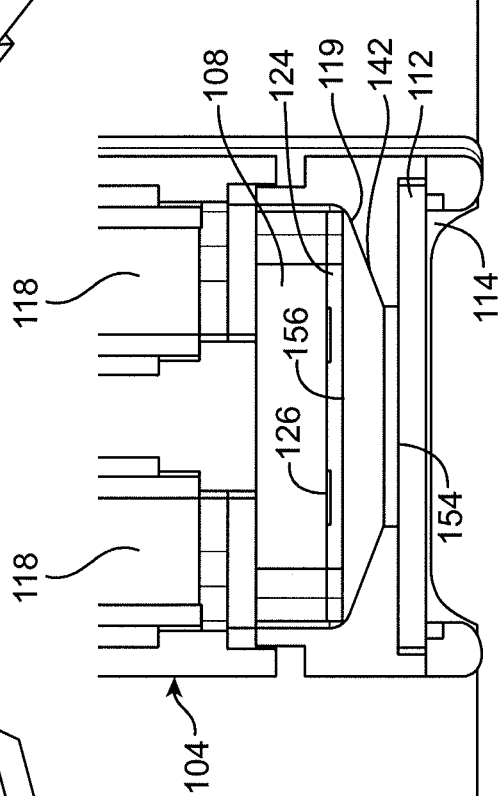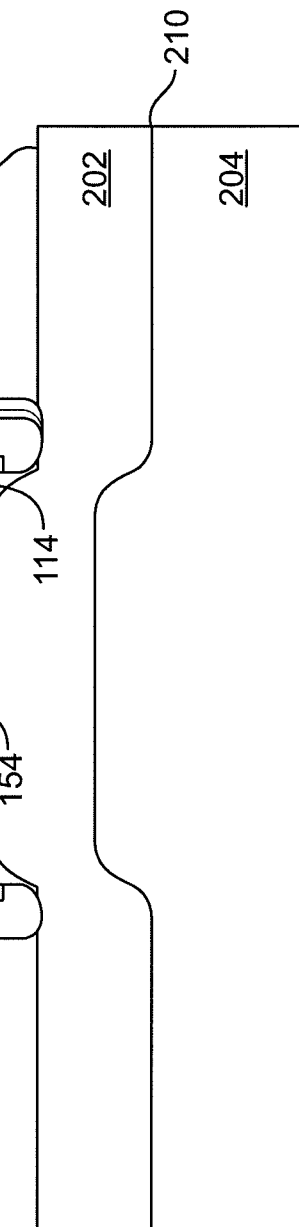

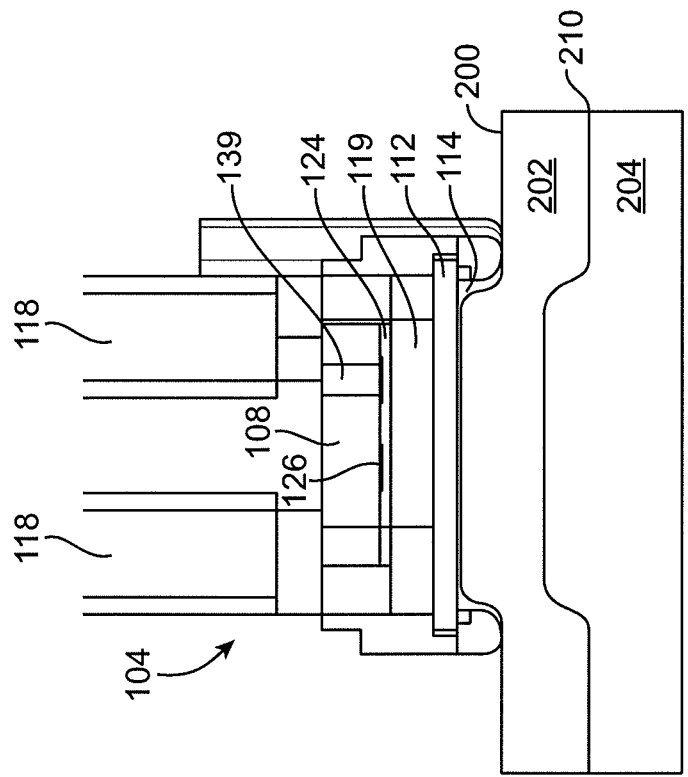
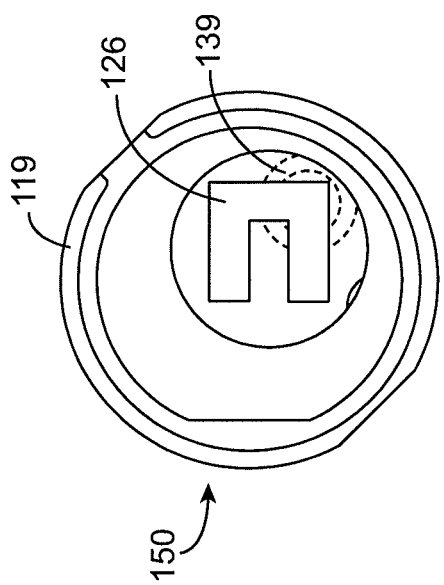
FIG. 9B
FIG. 9A

APPARATUS AND METHODS FOR THE TREATMENT OF TISSUE USING MICROWAVE ENERGY

CROSS-REFERENCE TO RELATED APPLICATIONS

This application claims the benefit under 35 U.S.C. 119 of U.S. Provisional Patent Application No. 61/858,050, filed Jul. 24, 2013, titled "Apparatus and Methods for the Treatment of Tissue Using Microwave Energy", which application is incorporated by reference as if fully set forth herein.

INCORPORATION BY REFERENCE

All publications and patent applications mentioned in this specification are herein incorporated by reference to the same extent as if each individual publication or patent application was specifically and individually indicated to be incorporated by reference.

FIELD

The present disclosure relates generally to thermal treatment of tissue. More specifically, the present disclosure relates to applying microwave energy to treat tissue.

BACKGROUND

Focused heat may be used for numerous purposes in dermatology. Such purposes include hair removal, sweat reduction, treatment of acne, treatment of toe nail fungus and other skin diseases. When using heat for the removal of unwanted hair, the primary target for heat-based hair removal is typically the bulb or the root of the hair follicle. The bulb is the deep, bulbous portion of the follicle that surrounds the dermal papilla. The bulb contains the matrix cells, the living, actively proliferating group of cells, which differentiate and become keratinized to form the hair cortex. As they grow and develop, these cells steadily push the previously formed cells upwards. When the cells reach the upper part of the bulb they begin to change and arrange themselves into six cylindrical layers, one inside the other. The inner three layers of cells become the actual hair. The outer three layers become the lining of the hair follicle—the inner root sheath. Heating the bulb to temperatures that cause cellular necrosis will render the matrix cells useless, thereby stopping hair growth. A secondary target in hair removal is the bulge of the hair follicle. The bulge is located in the isthmus, which is the region between the sebaceous gland and the erector pili muscle. The bulge region is believed to be the storage area for hair follicle stem cells. Hair follicles go through a cycle of growth, transition and rest. With each successive effort to produce hair fiber, the hair follicle must obtain a source of cells to form the matrix cell population that make hair fibers. The source of these cells is believed to be the bulge region. Heating the bulge to temperatures that cause cellular necrosis will likely prevent the hair follicle from regenerating. Alternative targets for the use of heat in dermatology include the sebaceous gland for the purpose of acne reduction, sweat glands, including those in the hands and feet, for the purpose of sweat reduction and toe nail beds for the purpose of reducing or eliminating toe nail fungus.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

FIG. 8A-8C illustrates a microwave applicator and components thereof with a tapered housing according to embodiments of the present invention.

FIG. 8A is a perspective view of the microwave applicator of FIG. 2A placed on skin tissue.

FIG. 8B is a perspective view of the housing of embodiments of the antenna assembly used in the microwave applicator of FIG. 8A.

FIG. 8C is a cutaway view of the applicator of FIG. 8A, applied to tissue.

FIGS. 9A and 9B illustrate an applicator design with a smaller opening and antenna assembly size.

FIG. 9A is a bottom view the housing and antenna assembly with a smaller opening.

FIG. 9B is a cutaway view showing the reduced size opening and antenna assembly in the microwave applicator of FIG. 2A.

FIG. 10A is a perspective view of a focusing element placed adjacent an antenna assembly according to embodiments of the present invention.

FIG. 10B is a side view of the embodiment of FIG. 10A showing the taper of a focusing element according to one embodiment of the present invention.

FIG. 10C cutaway view of an applicator including a tapered focusing element according to one embodiment of the present invention.

FIG. 11A is a top view of a splitting element placed adjacent to an antenna assembly according to embodiments of the present invention.

FIG. 11B is a side view of the embodiment of the invention illustrated in FIG. 11A.

FIG. 11C is a cutaway view of an applicator including a splitting element.

DETAILED DESCRIPTION

This disclosure, including the appendices, describes systems and methods for delivering microwave energy to the skin such that a focal zone of destructive heat is generated in the upper sub-dermis, mid-dermis, and/or lower dermis. This microwave therapy may be used for hair removal, treatment of acne, skin tightening, treatment of toe nail fungus or sweat reduction. In some embodiments of the present invention, the thermal zones per energy activation are relatively small. In embodiments of the invention, lesion dimensions will be less than the thickness of the skin, such as, for example, between approximately 1 and 2 millimeters. In some embodiments of the present invention, multiple energy activations may be delivered to fully or partially treat a patient in a given session.

Figure 1:
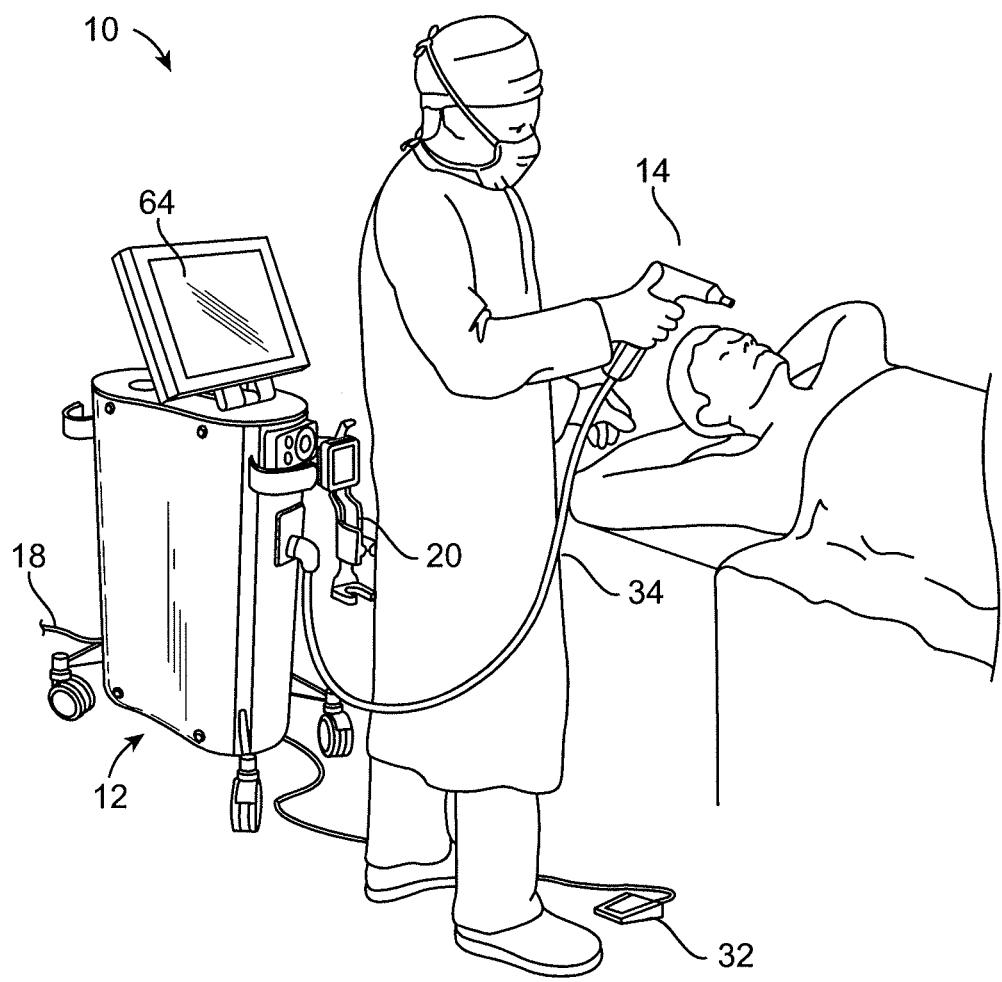
FIG. 1 illustrates a physician preparing to treat a patient using embodiments of a microwave therapy system according to the present invention.

FIG. 1 shows an embodiment of a system 10 for applying, in a non-invasive manner, microwave energy to a targeted tissue region. As shown in FIG. 1, the system 10 may include two main components; a system console 12 and a microwave applicator 14. The microwave applicator 14 may be coupled to the system console 12 with special purpose cable assembly 34, as shown. The system illustrated in FIG. 1 may further include holster 20, power cord 18, graphical user interface 64 and foot switch 32. System 10 may include a 5.8 GHz microwave energy source, a fluid cooling system, and a vacuum system (not shown).

In FIG. 1, the system 10 is particularly sized and configured to generate and apply microwave energy to skin tissue 200 of a patient. The system console 12 may be a durable item capable of repeated re-use. The system console 12 may comprise a cabinet or housing that is compact and capable of being wheeled for transport and positioning alongside the patient to be treated. Components housed within the console support specified treatment functions. An AC power cord 18 may couple components within the system console 12 to a standard AC power outlet. A power supply within the system console 12 may convert the power to 12V DC power for distribution to the components housed within the system console 12. System 10 may be an integrated control unit with a touch-screen user interface, including a touch-screen display, a microwave energy generator which provides microwave energy at a frequency of 5.8 GHz, a vacuum system with pump, reservoir, control valve and check valve, a cooling fluid 118 system with chiller/heat exchanger, pump, flow sensor and germicidal lamp, a control board, including integrated software, a medical grade power supply, an audible tone/alarm, and embedded software running on microprocessors. Components carried on-board system console 12 may be configured to generate an energy waveform selected to achieve the desired therapeutic objective in the targeted tissue region. These components may include a microwave generator and a master controller that includes preprogrammed rules or logic that set and/or vary the output power of the microwave generator according to the therapeutic objectives the system 10. The master controller may also include circuitry configured to implement a graphical user interface 64 on a display screen of system 10. In some embodiments of the present invention, the software may provide the user the ability to adjust the power, pre-cool time, energy delivery time, post-cool time and coolant temperature. The microwave generator, under the control of the master controller, may generate a microwave signal at the time of treatment. In some embodiments of the present invention, the microwave signal may lie in the ISM band of 5.725 to 5.875 GHz, with a frequency centered at approximately 5.8 GHz. Of course, other waveforms or variations in this waveform may be selected for generation by the waveform generation function. A microwave cable within special purpose cable assembly 34 is configured to couple the microwave signal to the microwave applicator 14.

The master controller of the system console 12 may set the power output for the microwave signal at between approximately 50 Watts and approximately 100 Watts, where the power output is measured into a 50 ohm load. As another example, the master controller may set a power output at approximately 90 Watts measured into a 50 ohm load. The power output may be matched to the impedance of the microwave applicator 14 and the special purpose cable assembly 34 to provide appropriate power out of the microwave applicator 14 at the frequency of interest.

The master controller of the system console 12 may also be configured to control the flow of cooling fluid 118 through cooling fluid conduits 117 and in/out of cooling chamber 110. The master controller may also be configured to control the application of vacuum from the vacuum source to the tissue acquisition chamber 114 to pull skin tissue 200 into contact with cooling plate 112. These cooling and vacuum functions may be performed automatically when microwave energy is applied from the microwave applicatory 14 to tissue of the patient. In some embodiments of the present invention, the master controller may be configured to apply pre-cooling and post-cooling to the skin tissue 200 for a period of time (such as, for example, between 0.2 seconds and 1 second) before and after the application of microwave energy.

The microwave applicator 14 may be disposable after each patient or treatment or a durable item capable of repeated re-use. The microwave applicator 14 may, in some embodiments of the present invention, include a disposable tip (such as, for example, acquisition chamber housing 140 with an integrated bio-barrier) adapted to protect the applicator tip from contamination with bodily fluids. As will be described in more detail below, the microwave applicator 14 may include one or more microwave antennas configured to deliver microwave energy to tissue. The microwave applicator 14 may be sized and configured to be, during use, conveniently handled and manipulated by a caregiver. When not in use, microwave applicator 14 may be may be conveniently rested in a holster 20 on the system console 12. In some embodiments of the present invention, the microwave applicator 14 may include a vacuum acquisition chamber 114, a surface cooling plate 112, a microwave antenna, and one or more thermocouple temperature sensors.

In some embodiments of the present invention, the microwave applicator 14 is a single antenna device with integrated cooling and vacuum features. Embodiments of the invention also include microwave applicators 14 without vacuum features. Vacuum features are particularly beneficial in some embodiments where the physician wishes to precisely control the cooling and microwave application time to a particular target tissue region. The vacuum features may be designed to acquire and position a particular tissue region such that it is immobilized in acquisition chamber 114 and does not move during treatment. Acquisition chamber 114 may be a shallow cavity within the distal treatment portion 104 of microwave applicator 14 where target tissue can be localized and stabilized for focused treatment. This can be particularly important where the treatment is dependent upon a precise time for cooling and/or microwave energy application. Once the skin is pulled into acquisition chamber 114, it is locked in place against cooling plate 112 and begins to cool. The distal surface of cooling plate 112 cools the upper dermis to protect the skin surface and upper dermis. System 10 may be programmed to provide for preset (or settable) pre-cool, energy application and post cool intervals to precisely control the depth and size of lesions created in the tissue.

Figure 2A:
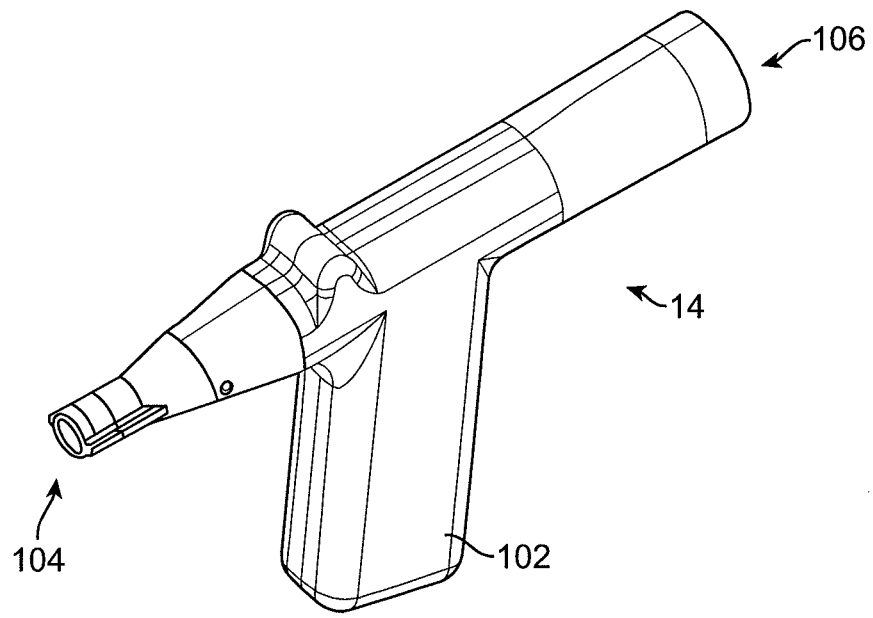
FIGS. 2A and 2B illustrate embodiments of microwave applicators according to the present invention.
Figure 2B:
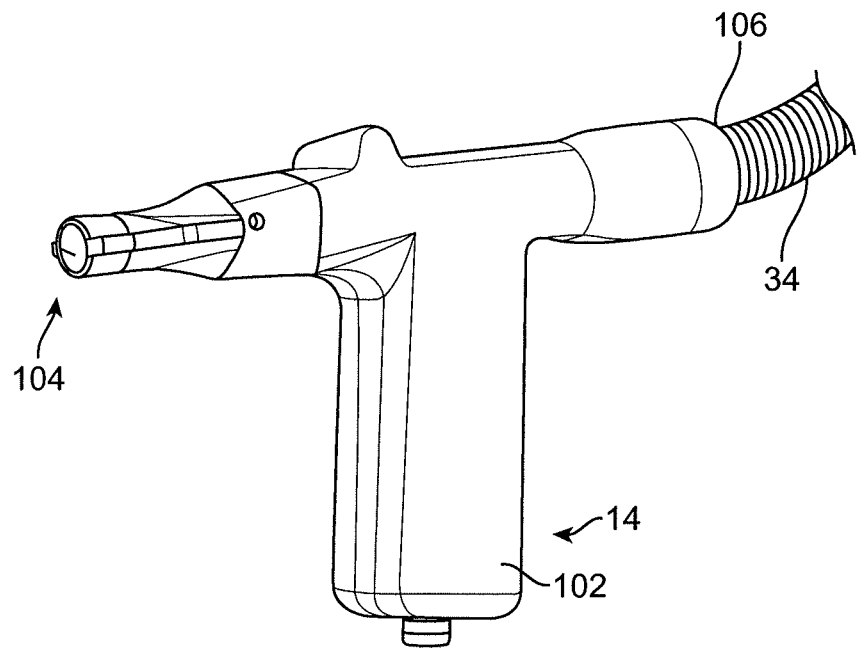

FIG. 2A is a schematic drawing of a microwave applicator 14, and FIG. 2B is a schematic drawing of an alternate embodiment of microwave applicator 14. Microwave applicator 14 may include a handle portion 102, a distal treatment portion 104, and a proximal portion 106. The handle portion 102 may be sized and configured to be grasped by a user during therapy. In some embodiments of the present invention, the handle portion 102 may include buttons or switches (not shown) to activate and deactivate microwave therapy from the microwave applicator 14. In other embodiments, activation and deactivation of the microwave therapy may be controlled from the system console 12 or by foot switch 32. The distal treatment portion 104 of the microwave applicator 14 may include at least one microwave antenna, a cooling system, and vacuum features, where the vacuum features are configured to couple the cooling system and/or microwave antenna(s) to the skin to be treated. The microwave applicator 14 may be attached to the system console 12 with a cable (e.g., cable assembly 34) at the proximal portion 106 of the applicator. Cable assembly 34 may include: a data cable, which may include thermocouple wires, for sending temperature information from thermocouple 122 on cooling plate 112 to system console 12; a coaxial cable to deliver energy from the console to the antenna; tubing for the vacuum system; and tubing for cooling fluid 118 circulation. In embodiments of the invention, the antenna may be an antenna assembly 150, such as, for example, antenna assembly 150

Figure 3C:
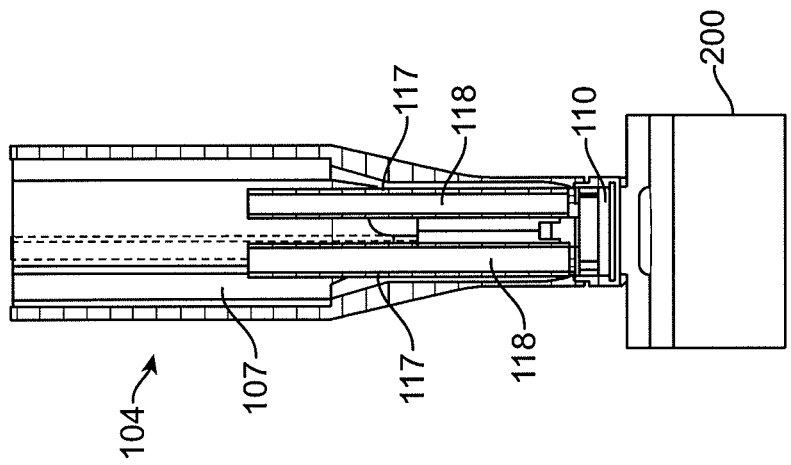
FIGS. 3A, 3B and 3C illustrate various views of a distal treatment portion of the microwave applicators of FIGS. 2A-2B according to embodiments of the present invention.
Figure 3B:
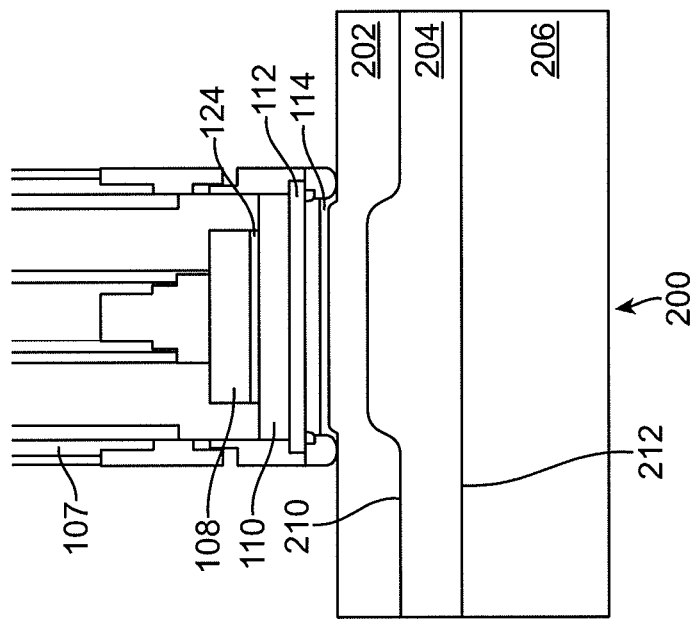
Figure 3A:
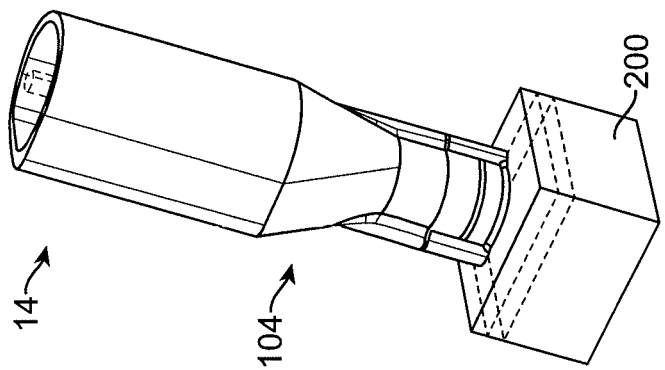

FIGS. 3A, 3B and 3C illustrate various views of distal treatment portions 104 of the microwave applicators 14 of FIGS. 2A-2B. FIG. 3A is a perspective view of the distal treatment portion 104 of microwave applicator 14, FIG. 3B is a zoomed-in cross-sectional view of the distal tip of distal treatment portion 104 and FIG. 3C is a cross-sectional view through the distal treatment portion 104 of the microwave applicator 14. In FIGS. 3A, 3B and 3C, the distal treatment portion 104 of microwave applicator 14 is engaged with skin tissue 200.

Referring to FIG. 3B, the distal tip of the distal treatment portion 104 may include antenna substrate 108 upon which a microwave antenna trace (which may also be referred to as 126 (which may also be referred to as a transmission line, microstrip or conducting trace) is mounted, a cooling chamber 110 configured to facilitate the flow of a cooling fluid 118 (e.g., deionized water, vegetable oil, saline or other coolant), a cooling plate 112 designed to come into thermal (e.g. direct) contact with skin tissue 200, and a tissue acquisition chamber 114 configured to pull skin tissue 200 into thermal contact with the cooling plate 112 through application of vacuum. In some embodiments of the present invention, the antenna substrate 108 may be a Rogers 6010.2 LM material, which has a dielectric constant of, for example, 10.2. In general a large dielectric constant decreases the wavelength and size of the antenna assembly 150 and its associated components. In some embodiments of the present invention, cooling chamber 110 and cooling fluid 118 may be separated from antenna substrate 108 and antenna trace 126 with a fluid barrier 124. Fluid barrier 124 may also be referred to as a cover layer, membrane, barrier membrane or superstrate. In some embodiments of the invention, fluid barrier 124 may be, for example, a plastic sheet, formed of, for example PET or UHMWPE film. In some embodiments of the invention, cooling chamber 110 may have a thickness of approximately 0.5 to 2 millimeters. In some embodiments of the invention, cooling plate 112 may have a thickness of approximately 0.25-1 millimeters. A vacuum conduit 107 may connect the acquisition chamber 114 to a vacuum source in system console 12 to provide the necessary vacuum to pull skin tissue 200 into contact with cooling plate 112. The vacuum source may be located externally to the microwave applicator 14 (e.g., in the system console 12) and may provide vacuum to the applicator through a vacuum tube in special purpose cable assembly 34. As illustrated in FIG. 3B, pulling skin tissue 200 into contact with cooling plate 112 stretches the region of the fat tissue 204 underlying the raised dermal tissue 202. In some embodiments of the present invention, this may create a change in the thickness of the fat tissue 204. In some embodiments of the present invention, this may create a change in the distance between tissue interfaces which reflect the incident wave, such as, for example, the distance between the dermal/hypodermal interface 210 and the fat/muscle interface 212 in the region underlying acquisition chamber 114.

Referring now to FIG. 3C, cooling fluid conduits 117 may connect the cooling chamber 110 to a cooling fluid 118 source in system console 12. Cooling fluid conduits 117 convey cooling fluid 118 to distal treatment portion 104 of microwave applicator 14. The cooling fluid 118 source may be located externally to the microwave applicator 14 (e.g., in the system console 12) and may deliver cooling fluid 118 to the cooling chamber 110 through special purpose cable assembly 34 of FIG. 1. During microwave therapy, cooling chamber 110 may be constantly supplied with fresh or recirculated cooling fluid 118 from system console 12 to control the temperature of cooling plate 112 which is in contact with skin tissue 200 in acquisition chamber 114. Since cooling plate 112 remains in thermal (e.g. direct or through a bio-barrier) contact with skin tissue 200 during therapy, cooling plate 112 is configured to prevent thermal injury to skin tissue 200 at or near the surface of skin tissue 200. Cooling plate 112 may be further configured to provide cooling to position a lesion 214 within skin tissue 200.

Figure 4A:
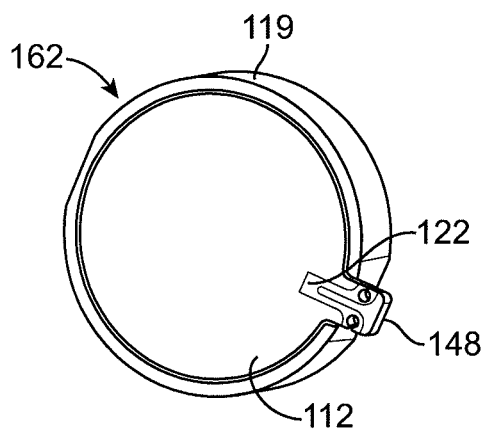
FIGS. 4AA, 4AB, 4B and 4C illustrate various views of assembly components of the microwave applicator according to embodiments of the invention, including cooling assembly, cooling plate, antenna assembly, antenna substrate and cooling chamber.
Figure 4A:
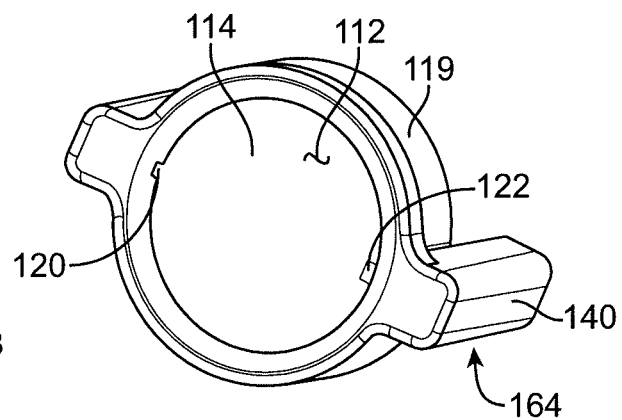

FIGS. 4AA, 4AB, 4B and 4C illustrate additional views of, cooling assembly 162, antenna substrate 108, cooling plate 112, and cooling chamber 110. FIG. 4AA is a distal end view of the tissue contacting portion of the cooling plate 112 with acquisition chamber housing 140 removed. The entire assembly, including antenna substrate 108, cooling plate 112, and cooling chamber 110, may be surrounded by antenna housing 119. Antenna housing 119 may comprise, for example, a metal material (such as, for example, stainless steel) and may be configured to reduce stray radiation from the microwave antenna. In some embodiments of the present invention, the antenna housing 119 may have an outer diameter of approximately 10 millimeters and a thickness of approximately 2 millimeters. In some embodiments of the invention, antenna housing 119 may include the walls of cooling chamber 110 as an integrated part of antenna housing 119.

In FIG. 4AA thermocouple 122 is positioned on cooling plate 112. Thermocouple 122, or other thermal sensors, may be positioned on cooling plate 112 to detect when proper skin acquisition has taken place prior to energy delivery. Thermocouple 122 may also be used to prevent or minimize burns on the skin surface by detecting temperatures beyond a set minimum and providing feedback to system 10. In some embodiments of the invention, cooling plate 112 may include, on its distal surface, a film (not shown), such as PET to provide electrical insulation between, for example, thermocouple 122 and tissue in applicator chamber 114. In FIG. 4AB, acquisition chamber housing 140 is positioned over antenna housing 119, antenna assembly 150 and cooling assembly 162 to form acquisition chamber 114. In FIG. 4AB vacuum port 120 in acquisition chamber housing 140 is adjacent cooling plate 112, connecting a vacuum source in system console 12 to acquisition chamber 114. In some embodiments of the invention, acquisition chamber housing 140 may be detachable from microwave applicator 14 to form a disposable element. In some embodiments of the invention acquisition chamber housing 140 may include a bio-barrier to prevent bodily fluids from reaching microwave applicator 14 and/or the distal surface of cooling plate 112.

Referring to FIG. 4AA and 4AB, vacuum may be pulled through the vacuum port 120 to pull skin tissue 200 into tissue acquisition chamber 114. In some embodiments of the present invention, thermocouple 122 on cooling plate 112 may be used to detect when proper skin acquisition has taken place prior to energy delivery, by, for example, detecting an increase in temperature when skin in acquisition chamber 114 comes into contact with thermocouple 122 and/or cooling plate 112. In some embodiments, as shown in FIG. 4AA and 4AB, vacuum port 120 may be placed generally on one side of cooling plate 112 with thermocouple(s) 122 placed on the opposite side. Since positions further away from vacuum port 120 (opposite the port) are generally the most difficult location to achieve tissue contact with cooling plate 112, this configuration ensures that an operator will know when there is good skin contact between the skin surface and cooling plate 112. Proper positioning may thus be ensured by monitoring the temperature at thermocouple 122 as that temperature will rise when thermocouple 122 comes in contact with skin tissue 200. A rise in temperature at thermocouple 122 may therefore be used by the system and/or operator as confirmation that skin tissue 200 is in proper contact with cooling plate 112. In another embodiment, thermocouple 122 may be placed at a location on the cooling plate the furthest possible distance from vacuum port 120. In some embodiments of the present invention, vacuum port 120 may be placed at a location on the cooling plate 112 along a line which extends from vacuum port 120 through the center of cooling plate 112. In some embodiments of the present invention, vacuum port 120 may be placed at a location on the cooling plate 112 along a line which extends from vacuum port 120 through the center of cooling plate 112 at a point near the edge of the acquisition chamber 114 opposite vacuum port 120.

In some embodiments of the invention, distal treatment portion 104 of microwave applicator 14 may include a cooling assembly 162. In some embodiments of the invention, a cooling assembly 162 may include cooling chamber 110, cooling plate 112, cooling fluid 118 and cooling fluid conduits 117. In some embodiments of the invention, cooling assembly 162 may further include cooling chamber 110. In some embodiments of the invention, cooling chamber 110 may be cylindrical. In some embodiments of the invention, cooling chamber 110 may include tapered cooling chamber walls 142 such that the diameter of a proximal taper opening 156 is larger than the diameter of a distal taper opening 154. In some embodiments of the invention, cooling chamber 110 may include a tapered focusing element 144. In some embodiments of the invention, cooling chamber 110 may include proximal taper wall 160 having a diameter greater than the diameter of a distal taper wall 158. In some embodiments of the invention, tapered focusing element 144 has a cone shape. In some embodiments of the invention, cooling chamber 110 may include a scattering element 146 (which may also be referred to as a splitting element). In some embodiments of the invention scattering element 146 may be cylindrical. In some embodiments or the invention scattering element 146 may include beveled edges 166 at a distal end thereof. In some embodiments of the invention, cooling plate 112 may include thermocouple 122. In some embodiments of the invention cooling fluid 118 may be an oil, such as, for example, vegetable oil. In some embodiments of the invention, cooling fluid 118 may be water. In some embodiments of the invention cooling fluid 118 may be deionized water.

Figure 4B:
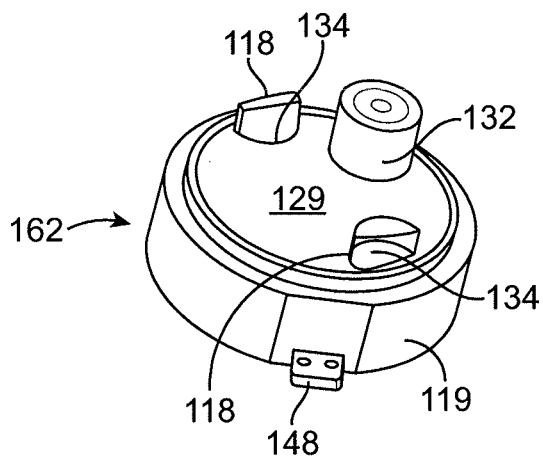
Figure 4C:
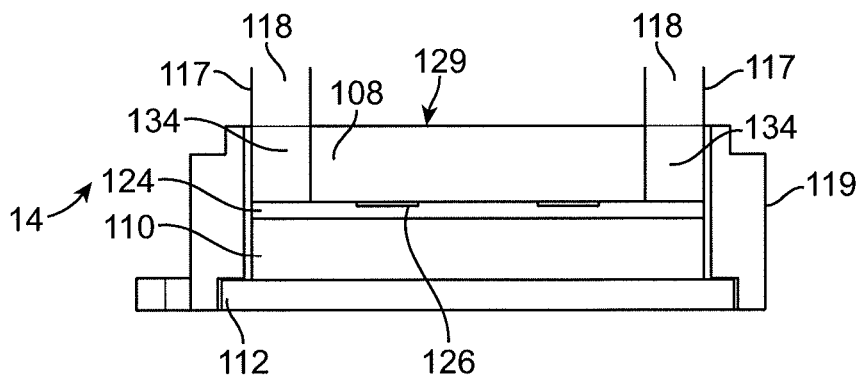

FIG. 4B shows a proximal (rear) view of the antenna housing 119 and ground plane 129, which may, in some embodiments be electrically connected (e.g. soldered) to antenna housing 119. In FIG. 4B, cooling fluid 118 may be seen flowing through cutouts 134 in antenna substrate 108 and ground plane 129. FIG. 4C is a cross-sectional view of distal treatment portion 104 with acquisition chamber housing 140 removed. FIG. 4C includes antenna housing 119, cooling plate 112, ground plane 129, cooling chamber 110, antenna substrate 108, cooling fluid 118 and fluid barrier 124. Fluid barrier 124 may be positioned between antenna substrate 108 and the cooling chamber 110. In FIG. 4C cooling fluid 118 flows through cooling fluid conduits 117 (not shown). In FIG. 4C, fluid barrier 124, which separates antenna substrate 108 from cooling chamber 110 may, for example, prevent antenna traces 126 positioned on antenna substrate 108 from contacting cooling fluid 118 in cooling chamber 110, preserving and/or enhancing fringing fields which are radiated by antenna trace 126. In some embodiments of the present invention, the addition of a fluid barrier 124 enhances the fringing fields of the antenna trace 126, thus enabling the antenna to radiate more efficiently. In some embodiments of the present invention, the addition of a fluid barrier 124 reduces attenuation of the fringing fields, thus enabling the antenna to radiate more efficiently. In some embodiments of the present invention, fluid barrier 124 may comprise a thin plastic material, such as a polyimide or polycarbonate. The dielectric constant of fluid barrier 124 may range from approximately 2.5 to approximately 4. In some embodiments of the present invention, fluid barrier 124 may be manufactured from low-loss dielectric materials, such as, for example, alumina, unclad circuit board or silicone. In some embodiments a parylene coating, Ultra-high-molecular-weight polyethylene (UHMWPE) material or silicone adhesive may be used to seal the antenna (e.g. to protect it from cooling fluids or prevent water ingress into critical components). In the embodiment of FIG. 4C, cooling fluid 118 flows into one side of cooling chamber 110, through cooling chamber 110 and out the opposite side of cooling chamber 110.

In some embodiments of the invention, distal treatment portion 104 of microwave applicator 14 may include a vacuum assembly 164. In some embodiments of the invention vacuum assembly 164 may include an acquisition chamber 114, a vacuum port 120 and a vacuum conduit 107. In some embodiments of the invention acquisition chamber housing 140 may for at least a part of vacuum assembly 164. Vacuum assembly 164 may further include a vacuum pressure sensor located at or near vacuum port 120. In some embodiments of the invention, a vacuum sensor located at or near vacuum port 120 may be used to detect acquisition of tissue in acquisition chamber 114. In some embodiments of the invention, a vacuum sensor located at or near vacuum port 120 may be used to detect sealing of tissue against cooling plate 112.

In the embodiment of the invention illustrated in FIG. 4C, distal treatment portion 104 may be constructed without vacuum features such as, for example, acquisition chamber housing 140, acquisition chamber 114 or vacuum conduit 107. In the embodiment of the invention illustrated, distal treatment portion 104 may be constructed without vacuum assembly 164. In this embodiment of the invention, a user may position the distal treatment portion 104 of microwave applicator 14 against the patient's skin such that cooling plate 112 is in thermal (e.g. direct) contact with the patient's skin prior to application of microwave energy. This embodiment of the invention provides the user with additional ways to apply the microwave energy, including moving the microwave applicator 14 continuously across the skin surface.

In some embodiments of the present invention, the thickness of fluid barrier 124 may be a critical dimension. In these embodiments, a large portion of the fringing fields radiated by antenna trace 126 exist in the fluid barrier 124. Thus changing the thickness of fluid barrier 124 may cause significant changes in the effective dielectric constant ($\varepsilon_{eff}$) of an antenna trace 126 positioned on antenna substrate 108. Any change in $\varepsilon_{eff}$ may also lead to a change in the effective wavelength of the antenna, potentially resulting in a change in the impedance of the antenna. For some embodiments of the present invention a fluid barrier 124 having a thickness of 0.254 millimeters may be optimal. If it were desirable to utilize a different thickness, the change in $\varepsilon_{eff}$ could be compensated for by, for example, adjusting the size of the antenna trace 126 or other elements of the antenna assembly 150 so that antenna assembly 150 still matched well with skin at the desired operating frequency, such as, for example, 5.8 GHz.

Figure 5A:
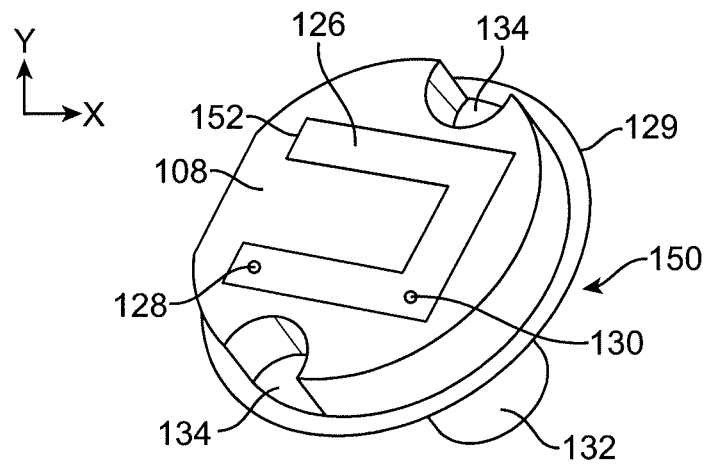
FIGS. 5A and 5B illustrate two views of an antenna assembly, antenna substrate and antenna trace of the microwave applicators of FIGS. 2A and 2B.
Figure 5B:
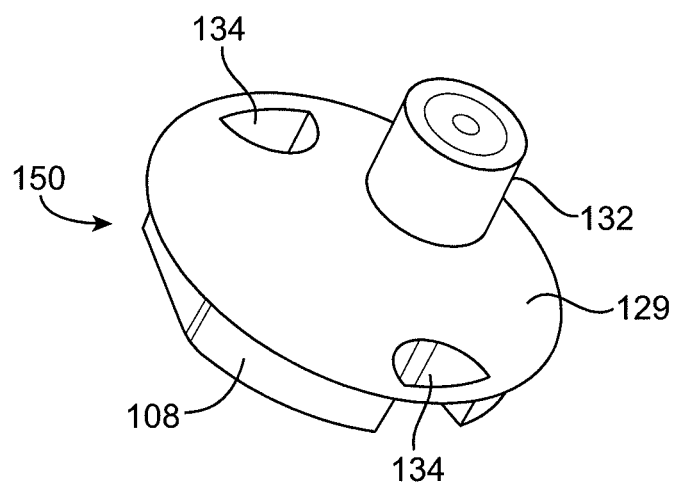

FIGS. 5A and 5B illustrate distal and proximal views, respectively, of embodiments of an antenna assembly 150 according to the present invention. In FIG. 5A, an antenna assembly 150 (which may be, for example, a patch antenna, such as, for example, a planar inverted-F type antenna (PIFA)), includes antenna trace 126 which is disposed on antenna substrate 108, by, for example, etching or plating. In some embodiments of the present invention, a thin spiral antenna trace 126 may be used, enabling a further size reduction. In some embodiments of the present invention antenna trace 126 may be formed of a metallic material and be fed at a feed point 130 with a micro-strip line or coaxial feed 132. The feed launches a signal into antenna trace 126 that travels from the feed point 130 to the edges of the trace, leading to fringing fields that are the source of radiation for the antenna. Typically, fringing radiation from multiple edges on antenna trace 126 will add in phase to create the most substantial portion of radiated energy. In FIGS. 5A-5B, cutouts 134 in antenna substrate 108 and ground plane 129 may be used to accommodate cooling fluid conduits 117 as they pass cooling fluids 118 through antenna assembly 150.

When designing the antenna assembly 150 of FIGS. 5A-5B, several design elements may be utilized to optimize the return-loss (match) at the frequency of interest, (e.g., 5.8 GHz) and the absorption pattern in tissue. Such design elements include the shape and size of the conducting trace, the feed and short locations, the circuit board material, the material and thickness of the plastic cover, the dimensions of the housing, and finally the routing of the water into the coolant chamber. In some embodiments of the present invention, shorting post 128 may be positioned in a region where minimizing the voltage on antenna trace 126 will not negate the desired fringing fields while optimizing the return-loss at the frequency of interest. In some embodiments of the present invention, the proximity of feed point 130 to shorting post 128 may be adjusted to match the antenna to a desired impedance (e.g. 50 ohms). In some embodiments of the invention, shorting post 128 may not be necessary and the impedance match achieved by appropriate design of other antenna features, including the length of antenna trace 126.

In some embodiments of the invention, a rectangular spiral shape as shown in FIG. 5A may be chosen as the geometry for antenna trace 126. In this embodiment, the number of turns of the spiral is less than one and may be approximately ¾ of a turn. In some embodiments of the invention, a small number of turns allows for a wider antenna trace 126 width (e.g., 1 millimeters) than might be utilized in a small form factor spiral with more turns, which is an important consideration for devices which may, in some embodiments of the present invention, be configured to operate at power levels of approximately 50 to 100 W. In some embodiments of the invention, high current densities present in narrower traces may cause undesirable antenna trace and antenna substrate 108 heating at high power levels. In some embodiments, antenna trace 126 may have patch dimensions of approximately 4 millimeters by 5 millimeters, with a trace width of approximately 1 millimeter. In some embodiments, the antenna trace 126 may have a trace length of approximately 5 millimeters along the x-axis and a trace length of approximately 1 millimeter along the y-axis. In some embodiments of the invention, such as, for example, where a small bandwidth is desirable, reducing the number of turns in the spiral trace will typically reduce the applicator bandwidth. In some embodiments of the invention the number of turns, width or length of antenna trace 126 may be modified to fine-tune the shape of the absorption pattern in skin. In further embodiments of the invention, other spiral shapes, such as circular may also be utilized for antenna trace 126.

In the embodiment of FIG. 5A, the feed point 130 may be placed at the lower right hand corner of the trace, and shorting post 128, which extends through antenna substrate 108 to ground plane 129, may be placed at the lower left hand corner of antenna trace 126. In some embodiments, the distance from feed point 130 to the open-circuit edge 152 of antenna trace 126 (upper left hand corner) may be set to approximately one-half wavelength at the frequency of interest (e.g. 5.8 GHz) and the distance from the feed point 130 to the shorting post 128 (lower left hand corner) may be set to approximately one-quarter wavelength at the frequency of interest (e.g. 5.8 GHz).

Figure 6:
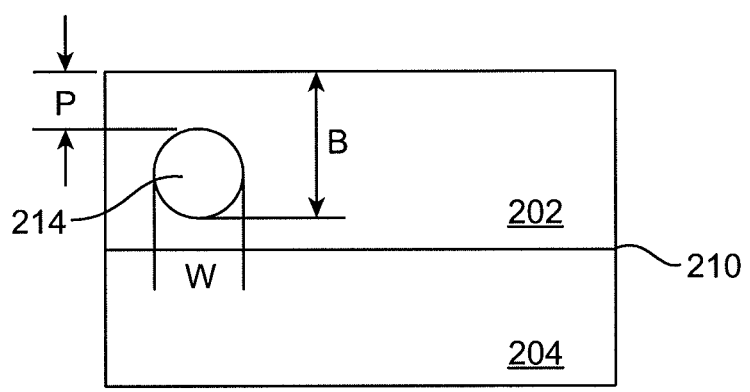
FIG. 6 is a diagram showing the location of a lesion created using a microwave applicator according to the present invention.

FIG. 6 is a diagram showing the location of a lesion 214 created by a microwave applicator 14 according to the present invention. Microwave applicator 14 is designed to deliver therapeutic heat to relatively small, shallow areas within the dermis and upper sub-dermis. In some embodiments of the invention, this may be achieved by utilizing short bursts, such as, for example, less than 1 second of energy. In some embodiments of the invention, the short burst of energy reduces or eliminates the pain felt by a patient, thus reducing or eliminating the need for injectable and/or topical anesthesia. Topical anesthesia may be used on patients that may not be able to tolerate the pain from the procedure. In some embodiments of the invention, larger areas of tissue may be treated, for example, by moving the applicator across tissue and repeating this procedure. In some embodiments of the invention, a template system may be used to guide the placements for a particular procedure.

In some embodiments of the invention, using suction created at system console 12, skin tissue 200 is first drawn into acquisition chamber 114 and held against the cooling plate 112. While the skin is in the chamber, microwave energy is delivered to the target site for the selected duration time. Following microwave energy delivery, the skin is cooled and then released from the chamber. An audible "treatment" tone may sound during this entire treatment cycle. In some embodiments of the invention, a treatment cycle may include three phases. In a first or acquisition and pre-cool phase, skin tissue 200 is acquired by applying vacuum and pre-cooling the skin when it comes into contact with the cooling plate 112. In a second or energy delivery phase microwave energy is delivered to the target skin tissue 200. In a third or post-cool phase, the treated skin is cooled by maintaining contact with the cooling plate 112. In some embodiments where vacuum is applied, it is applied through all three phases. In some embodiments of the invention, a single treatment cycle will treat an area of approximately 2 millimeters.

In some embodiments of the invention, microwave applicator 14 is adapted to deliver microwave energy to the skin such that a focal zone of destructive heat is generated in the mid to lower dermis, where the hair bulb, hair bulge, sebaceous gland, sweat glands or other target tissue may reside. In some embodiments of the invention the focal zone of destructive heat creates a thermal treatment zone to cause cellular necrosis in targets in the skin, such as the hair bulb, hair bulge. In some embodiments of the invention the thermal zones generated by individual energy activations will be small. In some embodiments of the invention lesion dimensions will be less than the thickness of the skin. In some embodiments of the invention lesion dimensions will be between approximately 1 and 2 millimeter. FIG. 6 represents a typical thermal lesion 214 created in skin tissue 200 by a system 10 according an embodiment of the present invention. In FIG. 6, distance P is the distance from surface of skin tissue 200 to the top of lesion 214. Distance B is the distance from the surface of skin tissue 200 to the bottom of lesion 214. Distance W is the width of lesion 214. In some embodiments of the invention P may range up to a depth of approximately 1.75 millimeters from the skin surface. In some embodiments of the invention, W may range up to a width of approximately 2.75 millimeters. In some embodiments of the invention B may range up to a depth of approximately 3.5 millimeters from the skin surface. In some embodiments of the invention, these results may be achieved using a microwave applicator 14 according to the present invention having the following settings, a power to microwave applicator 14 of approximately 90 Watts, a cooling fluid 118 temperature of, between approximately 10 and 15 degrees centigrade, a pre-cool time of between 0.2 and 1.0 seconds, an energy delivery time of between approximately 0.3 and 0.7 seconds and a post-cool time of between 0.2 and 1.0 seconds. In some embodiments of the present invention, the input power to microwave applicator 14 is measured using a 50 ohm load at system console 12. In some embodiments of the invention, tissue may be brought into contact with cooling plate 112 by application of a vacuum system and released from contact with cooling plate 112 by terminating the vacuum. In some embodiments of the invention, the magnitude of the vacuum may be, for example, −508 to −559 mm of Hg (−20 to −22 inches of Hg).

Figure 7:
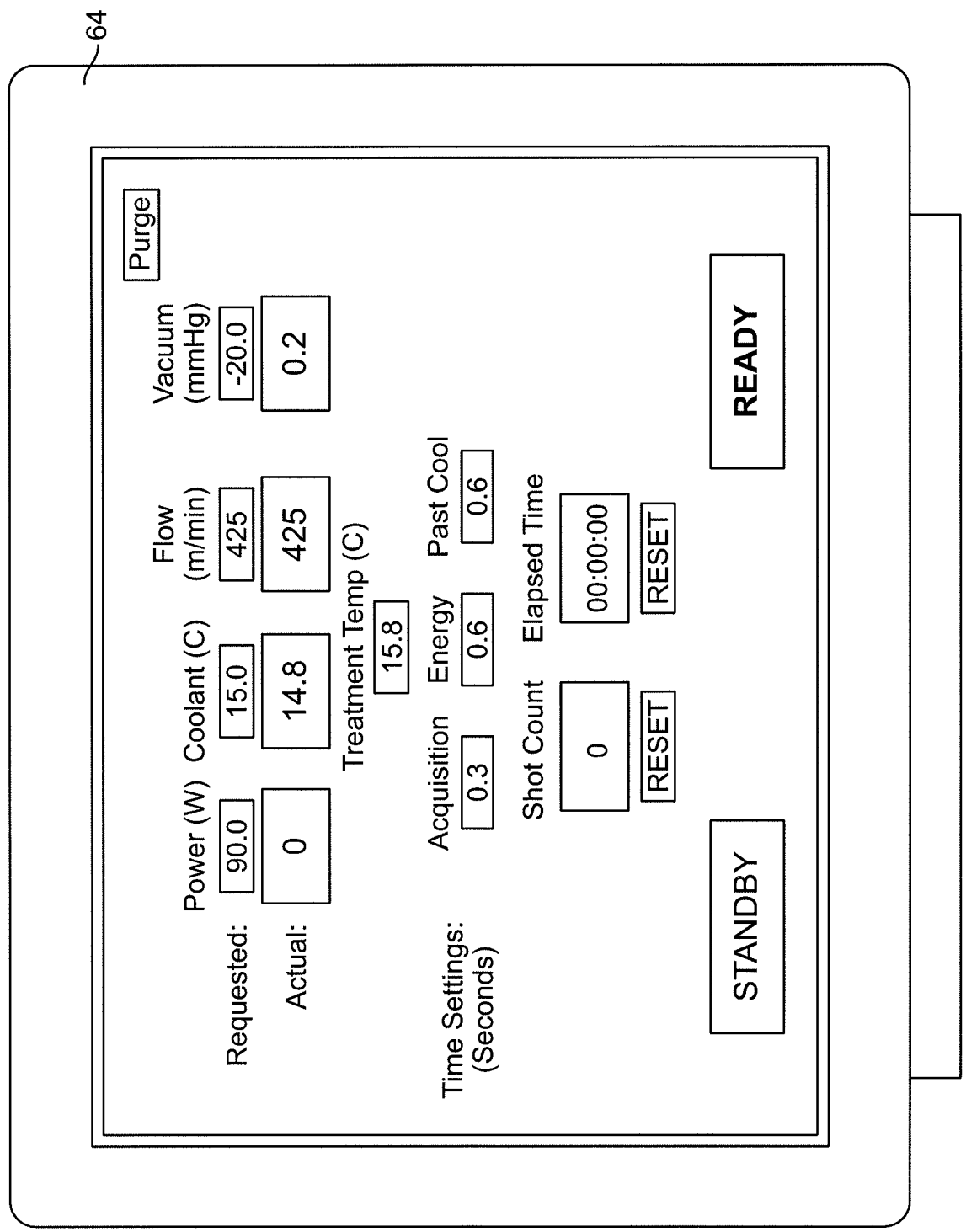
FIG. 7 shows an embodiments of a graphical User Interface to be displayed to a user of the system.

As illustrated in FIG. 7 graphical user interface 64 of system 10 may display and facilitate the adjustment of parameters of potential interest to the user, such as coolant flow rate, vacuum pressure, elapsed time, and shot (energy activation) counter. In some embodiments, a user can adjust the power, pre-cool time, energy delivery time, post-cool time and coolant temperature using graphical user interface 64.

FIG. 8A-8C illustrate a microwave applicator 14 with a tapered cooling chamber wall 142 according to embodiments of the present invention. In some embodiments of the invention the focusing effect of utilizing a tapered cooling chamber wall 142, reduces the lesion size by up to 75% over a microwave applicator 14 without a tapered cooling chamber wall 142. FIG. 8A is a perspective view of microwave applicator 14 placed on skin tissue 200. FIG. 8B is a perspective view of antenna housing 119 with tapered cooling chamber wall 142 according to embodiments of the invention. FIG. 8C is a cutaway view of the microwave applicator 14, applied to skin tissue 200. In FIGS. 8A-8C, the cooling chamber housing wall is tapered from a proximal taper opening 156 at the proximal end of cooling chamber 110 to a distal taper opening 154 at the distal end of cooling chamber 110. In some embodiments of the invention, cooling chamber housing wall is tapered from a proximal taper opening 156 of approximately 8 millimeters diameter to a distal taper opening 154 of approximately 4 millimeters diameter. In some embodiments proximal taper opening 156 is adjacent fluid barrier 124 and distal taper opening 154 is adjacent cooling plate 112. In some embodiments of the invention, the taper of tapered cooling chamber wall 142 focuses the radiated signal as it travels through the coolant to create a smaller area absorption zone in the target tissue. In some embodiments of the invention, the 8 millimeter diameter at proximal taper opening 156 allows the antenna to remain impedance matched at the frequency of interest (e.g. 5.8 GHz). The angle and size of the distal taper opening 154 may be varied to optimize the absorption pattern and, thus, the lesion size, in the target tissue.

FIGS. 9A and 9B illustrate a microwave applicator 14 design with a smaller opening in antenna housing 119 and antenna trace 126. FIG. 9A is a bottom view the antenna housing 119 and antenna trace 126. FIG. 9B is a cutaway view showing the reduced size housing and antenna in the microwave applicator 14 of FIG. 2A. In the embodiment illustrated in FIGS. 9A and 9B, a smaller absorption zone, resulting in a smaller lesion, is created by shrinking the size of antenna trace 126 and the size of antenna housing 119. In some embodiments of the invention, the material for fluid barrier 124 may be modified to improve the matching for the smaller antenna size. In some embodiments of the invention fluid barrier 124 may be a ceramic material with a dielectric constant (K) of approximately 10. In some embodiments of the invention where a smaller absorption zone is desired in the tissue, antenna trace 126 the outer dimensions of the patch may be approximately 3 millimeters by 3 millimeters with a trace width of approximately 1 millimeters.

Figure 10A:
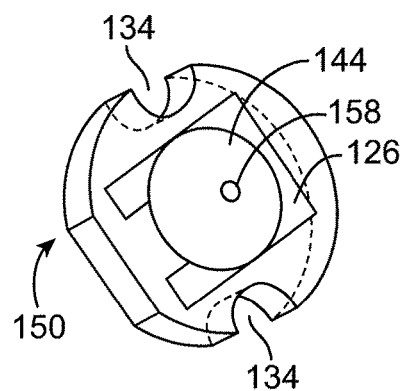
FIGS. 10A-10C illustrate a microwave applicator including a tapered focusing element according to embodiments of the present invention.
Figure 10B:
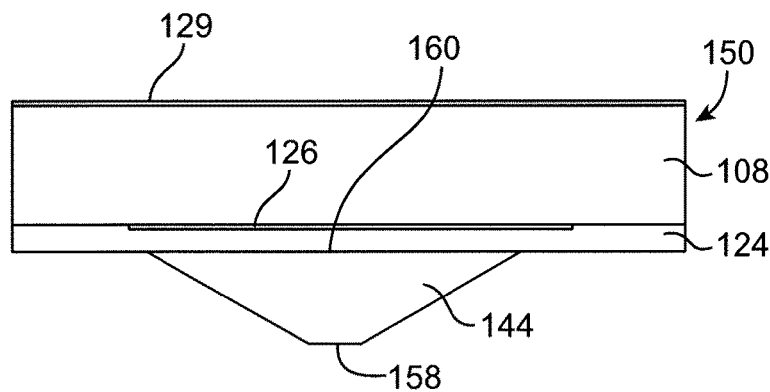
Figure 10C:
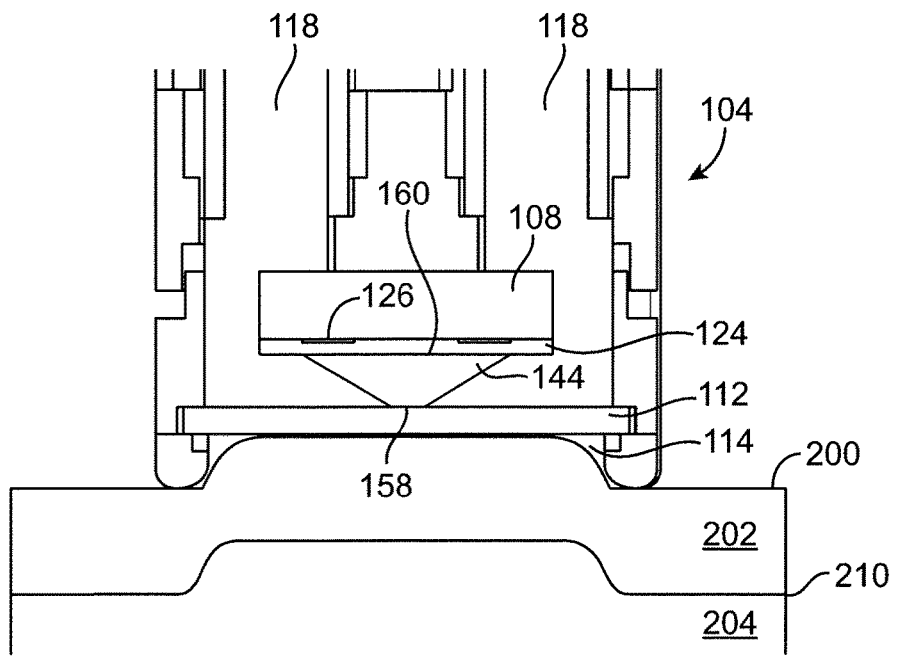

FIGS. 10A-10C illustrate a microwave applicator 14 including a tapered focusing element 144 according to embodiments of the present invention. In some embodiments of the invention utilizing a tapered focusing element 144, the focusing effect may reduce the lesion size by up to 75% over a microwave applicator 14 without a tapered focusing element 144. FIG. 10A is a perspective view of tapered focusing element 144 placed in cooling chamber 110 and against antenna assembly 150 according to embodiments of the present invention. FIG. 10B is a side view of the embodiment of FIG. 10A showing the taper of tapered focusing element 144. FIG. 10C is a cutaway view of a microwave applicator 14 including a tapered focusing element 144. In the embodiments of FIGS. 10A-10C, the taper is linear, with proximal taper wall 160 being approximately 4 millimeters in diameter and distal taper wall 158 being approximately 0.55 millimeters in diameter. In some embodiments, proximal taper wall 160 is placed against fluid barrier 124. In some embodiments, proximal taper wall 160 is positioned against antenna assembly 150 and distal taper wall 158 is positioned against cooling plate 112. In some embodiments, tapered focusing element 144 is 1 millimeter tall and extends through cooling fluid 118. In some embodiments of the invention, tapered focusing element 144 is manufactured from PD270 high dielectric constant ceramic from Pacific Ceramics, Sunnyvale Ca. In some embodiments, the tapered focusing element 144 may have a dielectric constant of approximately 270. In some embodiments the cooling fluid 118 may be a fluid (such as, for example, oil) having a dielectric constant (K) of between approximately 1 and 3. In some embodiments the cooling fluid 118 may be a fluid, such as, for example, oil having a dielectric constant (K) of approximately 2.33. In some embodiments cooling fluid 118 may be, for example, vegetable oils having a very low dielectric constant of, for example, around 3. The use of low dielectric cooling fluids 118, such as vegetable oils, may further enhance the contrast between cooling fluid 118 and tapered focusing element 144, reducing the size of the absorption area and any resulting lesion in the tissue.

In the embodiment of the invention illustrated in FIGS. 10A-10C tapered focusing element 144 is used to reduce the absorption area in skin tissue 200. In this embodiment, the microwave energy emitted by antenna trace 126 is focused by placing a tapered focusing element 144 in front of the antenna trace 126 where tapered focusing element 144 has a substantially larger dielectric constant then the surrounding cooling fluid 118. In this embodiment, the radiated signal tends to strike tapered focusing element 144 such that the fields at the edges tend to converge towards the center of tapered focusing element 144. In this embodiment of the invention the microwave energy is more narrowly focused within the skin to provide a smaller lesion. In the embodiment of FIGS. 10A-10C the size, position, taper angle and material of tapered focusing element 144 and cooling fluid 118 may be varied to tailor the resulting absorption pattern in the skin tissue 200. In an alternate embodiment, a cylindrical block having the characteristics and material construction of tapered focusing element 144 might also be used as an alternative focusing element.

Figure 11A:
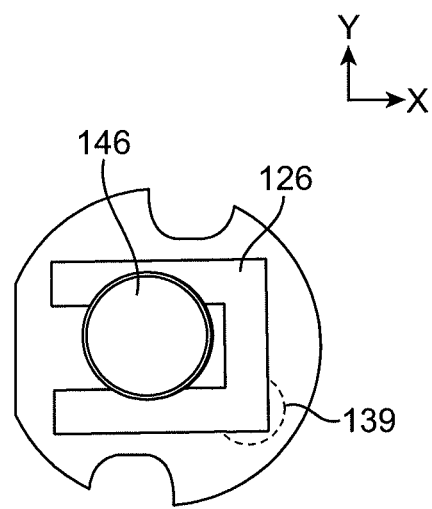
FIGS. 11A-11C illustrate a microwave applicator including a scattering element.
Figure 11B:
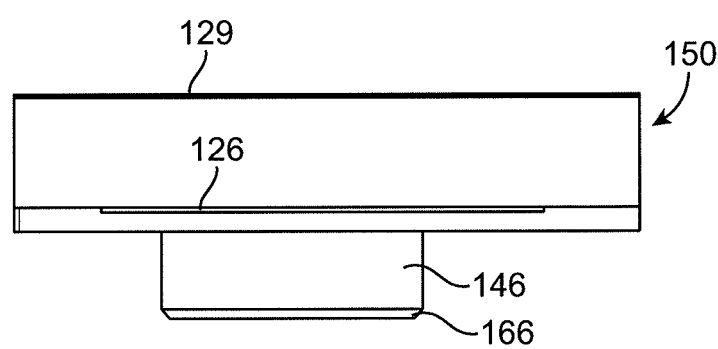
Figure 11C:
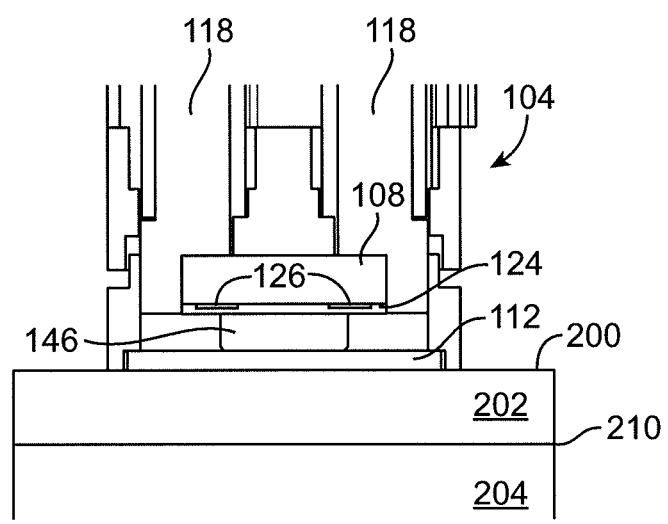

FIGS. 11A-11C illustrate a microwave applicator 14 including a scattering element 146. In some embodiments of the invention the scattering element 146 may be used to split the microwave field radiated by antenna trace 126 such that two small lesions are created where only a single, larger lesion would be created without scattering element 146. Such smaller lesions, may, for example, be useful in reducing the pain felt by a patient during the treatment. FIG. 11A is a top view of a scattering element 146 positioned in cooling chamber 110 according to embodiments of the present invention. FIG. 11B is a side view of the embodiment of the invention illustrated in FIG. 11A. FIG. 11C is a cutaway view of a microwave applicator 14 including a scattering element 146. In some embodiments of the invention scattering element 146 may be 3 millimeters in diameter. In some embodiments of the invention, scattering element 146 may be moved off of the centerline of antenna trace 126 to create a symmetric field split. In some embodiments of the invention, scattering element 146 may be moved off of the centerline of antenna trace 126 by a distance of, for example, −0.25 millimeters in the x direction and, for example, +0.25 millimeters in the y direction to create a symmetric split. In some embodiments, the movement of scattering element 146 is used to compensate for asymmetry in the radiation pattern of certain some embodiments of antenna assembly 150. In some embodiments of the present invention, scattering element 146 may be, for example, 1 millimeter tall and extend through the cooling fluid 118 to cooling plate 112. In some embodiments of the present invention of the invention, scattering element 146 may include a bevel 166 (which may also be referred to as a chamfer), such as, for example a 0.1 millimeter width bevel 166 to reduce high fields on sharp corners. In some embodiments of the present invention of the invention scattering element 146 may be metallic.

FIGS. 11A-11C illustrate a microwave applicator 14 with a scattering element 146 in front of antenna assembly 150. In this embodiment scattering element 146 is placed in front of the antenna trace 126 to scatter and spread out radiation as it travels out of antenna trace 126 and through cooling fluid 118. In this embodiment, a dramatic scattering affect may be created. In some embodiments, the scattering effect is created using a scattering element 146 with a much lower dielectric constant than the surrounding cooling fluid 118, which may be, for example, water. In another embodiment, scattering element 146 may be constructed of, for example, metal or a metallic material, which is very good at scattering the radiation emanating from antenna trace 126.

Referring again to FIG. 6, in one embodiment of the invention, the microwave applicator 14 is designed and configured to deliver therapeutic heat to relatively small (1-3 millimeters diameter), shallow areas (between 0-2 millimeters and 0-4 millimeters in depth) within the dermis and upper sub-dermis. The microwave energy may form standing waves in the tissue to heat and thermally damage tissue at specific depths in the dermis and/or fat. In some embodiments of the present invention it may be useful to utilize short bursts of energy to treat small areas within the dermis and/or fat. In some embodiments of the invention, the burst of energy may be approximately 2 seconds. In some embodiments of the invention, the burst of energy may be approximately 1 second. In some embodiments of the invention, the burst of energy may be approximately 0.7 seconds. In some embodiments of the invention, the burst of energy may be less than 0.5 seconds. In some embodiments of the present invention, short bursts of energy may substantially reduce or eliminate pain for the patient. In some embodiments of the present invention, the short burst of energy may eliminate the need for topical and/or injectable anesthesia.

In some embodiments of the invention, the interaction between incident waves transmitted directly from microwave applicator 14 and reflected waves may be used to generate a standing wave with a peak energy density in selected regions of the dermis. In some embodiments of the invention, energy transmitted directly from microwave applicator 14 may interact with energy reflected from the dermal/hypodermal interface to generate a standing wave with a peak energy density in a first region of the dermis. In some embodiments of the invention, energy transmitted directly from microwave applicator 14 may interact with energy reflected from the dermal/hypodermal interface and with energy reflected from the fat/muscle interface to generate a standing wave having a peak energy density in a second region of the dermis. In this embodiment, the addition of the second reflection moves the location of the peak energy density, and any associated lesion, to the second region. In some embodiments of the present invention, superposition of incident and reflected energy may be used to position a peak energy density at a desired position in skin, wherein the reflected energy may be reflected off one or more physical interfaces, including the dermal/hypodermal interface and other tissue interfaces within the skin, such as, for example, the fat/skeletal interface, the muscle/skeletal interface and/or the fat/muscle interface. In these embodiments, the peak energy density may be positioned at or near, for example, a sebaceous gland or a hair follicle, sweat gland, sebaceous gland or hair bulge (to eliminate stem cells). In some embodiments of the present invention of the invention the size and position of a lesion created by combining the incident and reflected waves may be further controlled by the temperature of the cooling plate 112. In some embodiments of the present invention of the invention, the size and position of a lesion 214 created by combining the incident and reflected waves may be further controlled by varying the duration of energy delivery. In some embodiments of the present invention of the invention, the size and position of a lesion 214 created by combining the incident and reflected waves may be further controlled by varying the duration of pre-cool and post-cool periods.

In some embodiments of the invention adjustment of the thickness of the fat layer underlying microwave applicator 14 by, for example, adjusting the amount of skin pulled into the acquisition chamber 114 may be used to adjust the position of the peak energy density by changing, for example, the distance between the dermal/hypodermal interface and the fat/muscle interface. In some embodiments of the invention, adjustment of the thickness of the fat layer underlying microwave applicator 14 may be used to adjust the depth of treatment. In some embodiments adjustment of the thickness of the fat layer underlying microwave applicator 14 may be used to adjust the depth of a lesion created by microwave applicator 14 in the dermis. In some embodiments adjustment of the thickness of the fat layer underlying microwave applicator 14 may be accomplished by, for example, adjusting the depth to which the skin tissue is pulled into the acquisition chamber 114. In some embodiments adjustment of the thickness of the fat layer underlying microwave applicator 14 may be accomplished by applying compression to the surface of the skin.

As described above, the systems and apparatus herein may be used to generate small lesions in tissue for hair removal, skin tightening, acne treatment, treatment of toe nail fungus or sweating (such as in the hands/feet). In some embodiments of the present invention, small lesions may be formed across the target tissue while leaving patches of healthy, untreated tissue in-between the lesions to promote healing.

According to one embodiment of the present invention, a method of creating a lesion in a region of skin tissue using a microwave applicator 14 includes the steps of: pulling the skin tissue into an acquisition chamber 114 at a distal end of the microwave applicator 14; raising the skin tissue in the acquisition chamber 114 a predetermined distance above the surface of the surrounding tissue such that the dermal/hypodermal interface underlying the applicator is moved toward the acquisition chamber 114; and modifying the predetermined distance to modify the depth of the lesion below the surface of the skin. In a further embodiment of the present invention, the method includes the step of adjusting the temperature of the tissue located in the acquisition chamber 114 to further modify the position of the lesion.

According to one embodiment of the present invention, a method of creating a lesion in tissue using a microwave applicator 14 includes the steps of: positioning skin tissue in an acquisition chamber 114 of the microwave applicator 14; radiating microwave energy into the skin tissue, the microwave energy having e-field and frequency characteristics which enable a first portion of the microwave energy to reflect off of a dermal/hypodermal interface in the tissue and a second portion of the microwave energy to reflect off of a fat/muscle interface in the tissue; creating a peak energy density region in the tissue by the super position of the incident radiation, the first reflected portion and the second reflected portion; and moving the position of the peak energy density region by modifying the depth of the tissue positioned in the acquisition chamber 114. In a further embodiment of the invention, the method includes the step of modifying the depth of the tissue in acquisition chamber 114 to modify the position of the dermal/hypodermal interface. In a further embodiment of the invention, the method includes the step of modifying the depth of tissue positioned in the acquisition chamber 114 to modify the distance between the dermal/hypodermal interface and the fat/muscle interface. In a further embodiment of the invention, the method includes the step of modifying the depth of the tissue positioned in the acquisition chamber 114 to change the distance the first and second reflected portions travel within the tissue.

According to one embodiment of the present invention a method of creating a lesion in a dermal layer of skin wherein the skin has at least a dermal layer and a sub-dermal layer includes the following steps: positioning a device adapted to radiate microwave energy adjacent an external surface of the skin; radiating microwave energy having an electric field component which is substantially parallel to a region of the external surface of the skin above the dermal layer, wherein the microwave energy has a frequency which generates a standing wave pattern of microwave energy in the dermal layer, the standing wave pattern having a constructive interference peak resulting from the superposition of an incident wave and at least two reflected waves, where a first reflected wave is reflected from a first tissue interface and a second reflected wave is reflected from a second tissue interface which is deeper in the skin than the first tissue interface. In a further embodiment of the invention the method includes the step of heating a portion of the dermal region in close proximity to the constructive interference peak interface using the radiated microwave energy to create the lesion. In a further embodiment of the invention, the method includes the step of adding a third reflective wave which contributes to the standing wave pattern, the third reflective wave reflecting off of a third tissue interface which is deeper than the second tissue interface. In a further embodiment of the invention, the first reflective interface is the interface between dermal and hypodermal tissue. In a further embodiment of the invention, the second reflective interface is the interface between hypodermal tissue and muscle. In a further embodiment of the invention, a third reflective wave contributes to the standing wave pattern, the third reflective wave reflecting off of a third tissue interface which is deeper than the second tissue interface. In a further embodiment of the invention, the second reflective interface is the interface between muscle and bone. In a further embodiment of the invention, the second reflective interface is the interface between hypodermal tissue and bone. In a further embodiment of the invention, the first reflective interface is the interface between dermal tissue and muscle. In a further embodiment of the invention, the second reflective interface is the interface between muscle and bone. In a further embodiment of the invention, the microwave energy is radiated as a fringing field. In a further embodiment of the invention, the microwave energy is radiated as a fringing field from an antenna trace on a patch antenna. In a further embodiment of the invention, the patch antenna is a planar inverted F antenna. In a further embodiment of the invention, the antenna trace is a spiral trace. In a further embodiment of the invention, the depth of the constructive interference peak is adjusted by changing the distance between the first tissue interface and the second tissue interface. In a further embodiment of the invention, the distance is changed by raising the skin surface. In a further embodiment of the invention, the skin surface is raised by pulling the skin into a vacuum chamber.

According to one embodiment of the present invention, a method of raising the temperature of at least a portion of a tissue structure located in a dermal layer of skin wherein the skin has at least a dermal layer and a sub-dermal layer, includes the steps of: positioning a device adapted to radiate microwave energy adjacent an external surface of the skin; radiating microwave energy having an electric field component which is substantially parallel to a region of the external surface of the skin above the dermal layer, wherein the microwave energy has a frequency which generates a standing wave pattern of microwave energy in the dermal layer, the standing wave pattern having a constructive interference peak resulting from the superposition of an incident wave and at least two reflected waves, where a first reflected wave is reflected from a first tissue interface and a second reflected wave is reflected from a second tissue interface which is deeper in the skin than the first tissue interface; and heating a portion of the dermal region in close proximity to the constructive interference peak interface using the radiated microwave energy to create the lesion. In a further embodiment of the invention, a third reflective wave contributes to the standing wave pattern, the third reflective wave reflecting off of a third tissue interface which is deeper than the second tissue interface. In a further embodiment of the invention, the first reflective interface is the interface between dermal and hypodermal tissue. In a further embodiment of the invention, the second reflective interface is the interface between hypodermal tissue and muscle. In a further embodiment of the invention, a third reflective wave contributes to the standing wave pattern, the third reflective wave reflecting off of a third tissue interface which is deeper than the second tissue interface. In a further embodiment of the invention, the second reflective interface is the interface between muscle and bone. In a further embodiment of the invention, the second reflective interface is the interface between hypodermal tissue and bone. In a further embodiment of the invention, the first reflective interface is the interface between dermal tissue and muscle. In a further embodiment of the invention, the second reflective interface is the interface between muscle and bone. In a further embodiment of the invention, the microwave energy is radiated as a fringing field. In a further embodiment of the invention, the microwave energy is radiated as a fringing field from an antenna trace on a patch antenna. In a further embodiment of the invention, the patch antenna is a planar inverted F antenna. In a further embodiment of the invention, the antenna trace is a spiral trace.

According to one embodiment of the present invention, a microwave medical device includes an applicator having a distal end effector including: an antenna including an antenna substrate 108, the antenna substrate 108 including a ground plane 129 on a first surface and a spiral trace on a second side thereof; a housing, a proximal end of the housing surrounding at least a portion of the antenna substrate 108, wherein the spiral trace is positioned in the interior of the housing and the ground plane 129 is positioned outside of, and connected electrically to, the housing; a cooling plate 112 positioned in the housing opposite the antenna substrate 108, the cooling plate 112 including a vacuum conduit 107 and a thermocouple 122 on a distal side, the distal side being positioned outside of the housing; a cooling fluid 118 positioned in the housing between the antenna trace and the cooling plate 112; and an acquisition chamber 114 surrounding the cooling plate 112 and including an opening at a distal end thereof. In a further embodiment of the invention, the antenna trace is optimized to operate at 5.8 GHz. In a further embodiment of the invention, the distal end effector further comprises a barrier positioned between the spiral trace and the cooling fluid 118. In a further embodiment of the invention, the spiral trace comprises an antenna having a feed and a short, the feed being located along a first arm of the spiral trace at a position approximately one-half wavelength from at least one open circuit edge 152 of the trace at the frequency of interest. In a further embodiment of the invention, the distance between the short and the feed is approximately one quarter wavelength. In a further embodiment of the invention, the number of turns in the spiral trace is approximately three quarters of a full turn. In a further embodiment of the invention, the antenna is an inverted-F type antenna.

According to one embodiment of the present invention, a microwave therapy device includes a ground plane 129; an antenna substrate 108 mounted on the ground plane 129; an antenna trace disposed on the antenna substrate 108; a cooling chamber 110 and cooling plate 112 disposed near the antenna, the cooling chamber 110 configured to hold a cooling fluid 118 to extract heat from the cooling plate 112; a tissue acquisition chamber 114 configured to apply vacuum to skin tissue to pull skin tissue against the cooling plate 112; and a microwave generator coupled to the antenna, the microwave generator configured to generate a microwave signal with the antenna to form lesions in or below the skin tissue.

According to one embodiment of the present invention, a microwave applicator 14 includes a distal treatment portion 104, the distal treatment portion 104 including: in some embodiments of the invention, a vacuum assembly 164; an antenna assembly 150; and a cooling assembly 162. In a further embodiment of the invention, the vacuum assembly 164 including: an acquisition chamber 114, wherein the cooling plate 112 forms a proximal wall of the acquisition chamber 114; and a vacuum port 120 connecting the acquisition chamber 114 to a vacuum conduit 107. In a further embodiment of the invention, the antenna assembly 150 comprises a patch antenna. In a further embodiment of the invention, the cooling assembly 162 includes: a cooling chamber 110; a cooling plate 112 at a distal end of the cooling chamber 110; cooling fluid 118 in the cooling chamber 110; and cooling fluid conduits 117 connected to the cooling chamber 110 to supply the cooling fluid 118 to the cooling chamber 110. In a further embodiment of the invention, the cooling chamber 110 has a cylindrical shape. In a further embodiment of the invention, the cooling chamber 110 has a tapered shape and including a proximal opening and a distal opening wherein the proximal opening is larger than the distal opening. In a further embodiment of the invention, the cooling chamber 110 having a cylindrical shape and including a proximal opening and a distal opening and a tapered focusing element 144 positioned in the cooling chamber 110 wherein the tapered focusing element 144 has a proximal taper wall 160 and a distal taper wall 158, the proximal taper wall 160 having a diameter greater than a diameter of the distal taper wall 158. In a further embodiment of the invention, the cooling chamber 110 has a cylindrical shape and including a proximal opening and a distal opening and a cylindrical scattering element 146 positioned in the cooling chamber 110. In a further embodiment of the invention, the patch antenna is a planar inverted F antenna. In a further embodiment of the invention, the patch antenna includes an antenna trace. In a further embodiment of the invention, the antenna trace is formed in a spiral shape. In a further embodiment of the invention, the spiral is a ¾ turn spiral. In a further embodiment of the invention, the patch antenna includes an antenna trace. In a further embodiment of the invention, the spiral is a rectangular spiral. In a further embodiment of the invention, the patch antenna includes an antenna trace 126, an antenna substrate 108 and a ground plane 129. In a further embodiment of the invention, a fluid barrier 124 is positioned between the patch antenna and the cooling chamber 110.

The foregoing description is as illustrative only of the principles of the invention. Furthermore, since numerous modifications and changes will readily occur to those skilled in the art, it is not desired to limit the invention to the exact construction and operation shown and described. While the preferred embodiment has been described, the details may be changed without departing from the invention, which is defined by the claims.

What is claimed is:

1. A microwave applicator (14), comprising a distal treatment portion (104) configured to attach to a handle portion (102), the distal treatment portion (104) comprising:
   an antenna housing (119);
   a cooling assembly (162) disposed in the antenna housing (119), the cooling assembly (162) comprising;
      a cooling chamber (110);
      a cooling plate (112) at a distal end of the cooling chamber (110);
      cooling fluid (118) in the cooling chamber (110);
      cooling fluid conduits (117) connected to the cooling chamber (110) to supply the cooling fluid (118) to the cooling chamber (110);
   a vacuum assembly (164) disposed in the antenna housing (119), the vacuum assembly (164) comprising:
      an acquisition chamber (114), wherein the cooling plate (112) forms a proximal wall of the acquisition chamber (114);
      a vacuum port (120) connecting the acquisition chamber (114) to a vacuum conduit (107);
   an antenna assembly (150) disposed in the antenna housing (119), the antenna assembly (150) comprising:
      an antenna substrate (108);
      a patch antenna disposed on the antenna substrate (108);
      cutouts (134) in the antenna substrate configured to accommodate the cooling fluid conduits to pass cooling fluid through the antenna assembly.

2. A microwave applicator (14) according to claim 1 wherein the patch antenna comprises a planar inverted F antenna.

3. A microwave applicator (14) according to claim 1 wherein the patch antenna comprises an antenna trace (126).

4. A microwave applicator (14) according to claim 3 wherein the antenna trace (126) is formed in a spiral shape.

5. A microwave applicator (14) according to claim 4 wherein the spiral shape is a ¾ turn spiral.

6. A microwave applicator (14) according to claim 4 wherein the spiral shape is a rectangular spiral.

7. A microwave applicator (14) according to claim 1 wherein the patch antenna comprises the antenna trace (126), the antenna substrate (108) and a ground plane (129).

8. A microwave applicator (14) according to claim 1 wherein a fluid barrier (124) is positioned between the patch antenna and the cooling chamber (110).

9. A microwave applicator (14) according to claim 1, wherein the antenna housing comprises a metal material configured to reduce stray radiation from the patch antenna.

* * * * *